(12) United States Patent
Axelson, Jr. et al.

(10) Patent No.: US 9,937,058 B2
(45) Date of Patent: Apr. 10, 2018

(54) PROSTHETIC IMPLANT AND METHOD OF IMPLANTATION

(71) Applicant: Stryker Corporation, Kalamazoo, MI (US)

(72) Inventors: Stuart L. Axelson, Jr., Austin, TX (US); Michael C. Ferko, Warwick, NY (US); Peter John Wellings, Somerset, NJ (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/163,146

(22) Filed: May 24, 2016

(65) Prior Publication Data

US 2016/0262910 A1      Sep. 15, 2016

Related U.S. Application Data

(63) Continuation of application No. 13/530,927, filed on Jun. 22, 2012, now Pat. No. 9,381,085.

(Continued)

(51) Int. Cl.
*A61F 2/30* (2006.01)
*A61B 34/00* (2016.01)
(Continued)

(52) U.S. Cl.
CPC .......... *A61F 2/461* (2013.01); *A61B 17/1675* (2013.01); *A61F 2/30771* (2013.01);
(Continued)

(58) Field of Classification Search
CPC ...... A61F 2/28; A61F 2/30; A61F 2/32; A61F 2/34; A61F 2/36; A61F 2/3601; A61F 2/3603; A61F 2/3804; A61F 2/3859; A61F 2/40; A61F 2/4014; A61F 2/4081; A61F 2002/285; A61F 2002/30159; A61F 2002/30337; A61F 2002/30377; A61F 2002/3611; A61F 2002/30889; A61F 2002/30891; A61F 2002/3859; A61F 2002/4014; A61F 2220/00; A61F 2220/0008
See application file for complete search history.

(56) References Cited

U.S. PATENT DOCUMENTS

| 4,085,466 A | 4/1978 | Goodfellow et al. |
| 4,550,448 A | 11/1985 | Kenna |

(Continued)

FOREIGN PATENT DOCUMENTS

| EP | 0028546 A1 | 5/1981 |
| WO | 2011072235 A2 | 6/2011 |

OTHER PUBLICATIONS

International Search Report and written opinion for Application No. PCT/US2012/043780 dated Aug. 23, 2012.

(Continued)

*Primary Examiner* — Thomas J Sweet
*Assistant Examiner* — Christie Bahena
(74) *Attorney, Agent, or Firm* — Lerner, David, Littenberg, Krumholz & Mentlik, LLP

(57) ABSTRACT

A prosthetic implant useful in a cementless application is disclosed. The implant may include a curved bone facing surface and one or more pegs or keels. Preferably, the implant is implanted on a bone surface that has been prepared so as to allow for a snap fit between the implant and the bone.

17 Claims, 52 Drawing Sheets

Related U.S. Application Data

(60) Provisional application No. 61/500,257, filed on Jun. 23, 2011.

(51) Int. Cl.

| | | |
|---|---|---|
| *A61B 17/16* | (2006.01) | |
| *A61F 2/38* | (2006.01) | |
| *A61F 2/46* | (2006.01) | |
| *A61F 2/40* | (2006.01) | |

(52) U.S. Cl.
CPC ............ *A61F 2/389* (2013.01); *A61F 2/3859* (2013.01); *A61F 2/3877* (2013.01); *A61B 34/00* (2016.02); *A61F 2/4081* (2013.01); *A61F 2002/30889* (2013.01); *A61F 2002/30891* (2013.01); *A61F 2002/3895* (2013.01)

(56) References Cited

U.S. PATENT DOCUMENTS

| | | | |
|---|---|---|---|
| 4,986,833 | A | 1/1991 | Worland |
| 5,593,448 | A | 1/1997 | Dong |
| 5,755,803 | A | 5/1998 | Haines et al. |
| 6,165,221 | A | 12/2000 | Schmotzer |
| 6,197,064 | B1 | 3/2001 | Haines et al. |
| 6,204,620 | B1 | 3/2001 | McGee et al. |
| 6,313,595 | B2 | 11/2001 | Swanson et al. |
| 6,322,567 | B1 | 11/2001 | Mittelstadt et al. |
| 6,364,910 | B1 | 4/2002 | Shultz et al. |
| 6,540,786 | B2 | 4/2003 | Chibrac et al. |
| 6,612,449 | B1 | 9/2003 | Otani et al. |
| 6,676,669 | B2 | 1/2004 | Charles et al. |
| 6,702,805 | B1 | 3/2004 | Stuart |
| 6,723,106 | B1 | 4/2004 | Charles et al. |
| 6,757,582 | B2 | 6/2004 | Brisson et al. |
| 6,916,341 | B2 | 7/2005 | Rolston |
| 7,035,716 | B2 | 4/2006 | Harris et al. |
| 7,160,330 | B2 | 1/2007 | Axelson, Jr. et al. |
| 7,294,149 | B2 | 11/2007 | Hozack et al. |
| 7,387,644 | B2 | 6/2008 | Beynnon et al. |
| 7,458,991 | B2 | 12/2008 | Wang et al. |
| 7,465,320 | B1 | 12/2008 | Kito et al. |
| 7,520,901 | B2 | 4/2009 | Engh et al. |
| 7,524,334 | B2 | 4/2009 | Haidukewych |
| 7,537,664 | B2 | 5/2009 | O'Neill et al. |
| 7,544,209 | B2 | 6/2009 | Lotke |
| 7,582,118 | B2 | 9/2009 | Brown et al. |
| 7,618,451 | B2 | 11/2009 | Berez et al. |
| 7,628,817 | B1 | 12/2009 | Axelson, Jr. et al. |
| 7,674,426 | B2 | 3/2010 | Grohowski, Jr. |
| 7,725,162 | B2 | 5/2010 | Malackowski et al. |
| 7,766,913 | B2 | 8/2010 | Bennett et al. |
| 7,831,292 | B2 | 11/2010 | Quaid et al. |
| 7,892,243 | B2 | 2/2011 | Stuart |
| 7,935,150 | B2 | 5/2011 | Carignan et al. |
| 8,002,777 | B2 | 8/2011 | Fox et al. |
| 8,004,229 | B2 | 8/2011 | Nowlin et al. |
| 8,010,180 | B2 | 8/2011 | Quaid et al. |
| 8,728,167 | B2 | 5/2014 | Collazo |
| 2003/0005786 | A1 | 1/2003 | Stuart et al. |
| 2005/0125068 | A1 | 6/2005 | Hozack et al. |
| 2006/0147332 | A1 | 7/2006 | Jones et al. |
| 2006/0228247 | A1 | 10/2006 | Grohowski |
| 2007/0100462 | A1 | 5/2007 | Lang et al. |
| 2008/0183177 | A1 | 7/2008 | Fox et al. |
| 2008/0188942 | A1 | 8/2008 | Brown et al. |
| 2008/0202274 | A1 | 8/2008 | Stuart |
| 2010/0094429 | A1 | 4/2010 | Otto |
| 2010/0222781 | A1 | 9/2010 | Collazo et al. |
| 2010/0268249 | A1 | 10/2010 | Stuart |
| 2010/0268250 | A1 | 10/2010 | Stuart et al. |
| 2010/0275718 | A1 | 11/2010 | Stuart et al. |
| 2010/0292804 | A1 | 11/2010 | Samuelson |
| 2010/0312348 | A1 | 12/2010 | Wang et al. |
| 2011/0087332 | A1 | 4/2011 | Bojarski et al. |
| 2011/0251694 | A1 | 10/2011 | Wasielewski |
| 2012/0109324 | A1 | 5/2012 | Keggi et al. |

OTHER PUBLICATIONS

Singer, G., Sep. 19, 2006, High-tech 3-d Knee Surgery. "A Company's Robot Installs Implants While a Monistor Positions them During . . . "
U.S. Appl. No. 61/530,614, filed Nov. 16, 2011.

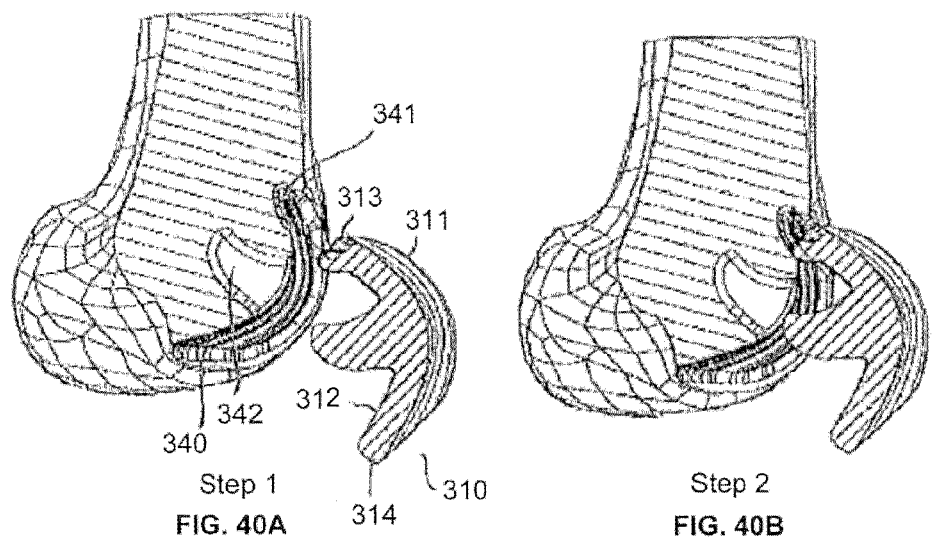
Step 1
FIG. 40A
Step 2
FIG. 40B
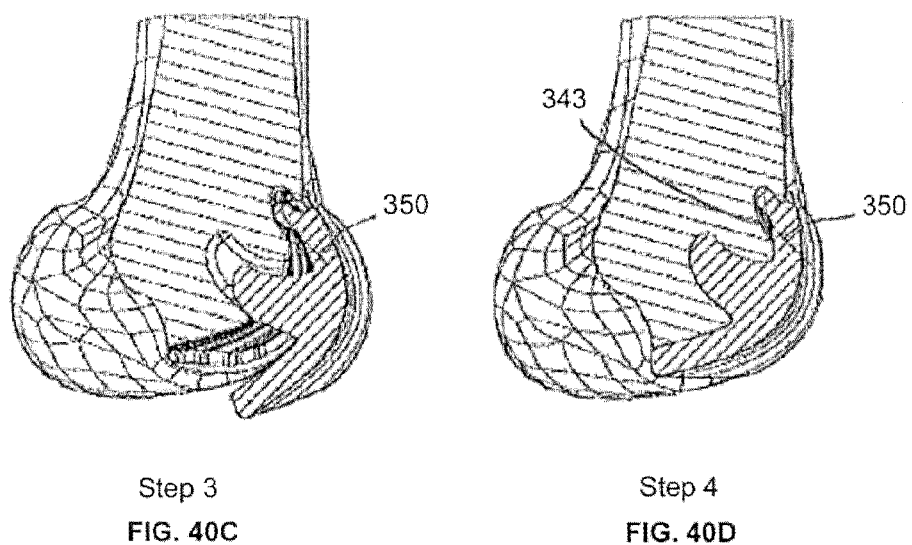
Step 3
FIG. 40C
Step 4
FIG. 40D Step 1

Step 2

Step 3

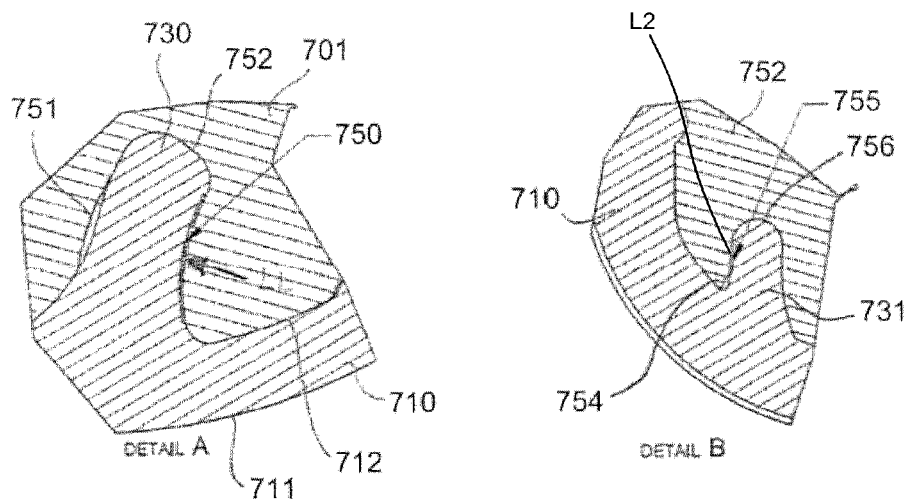
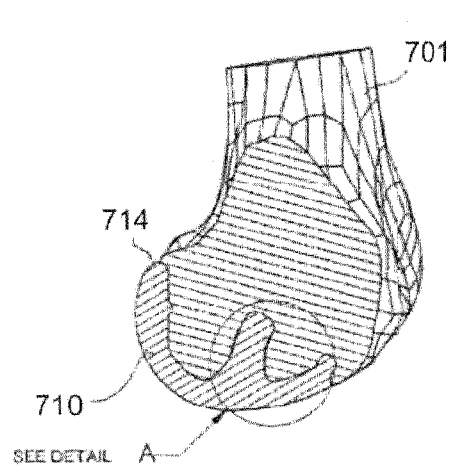
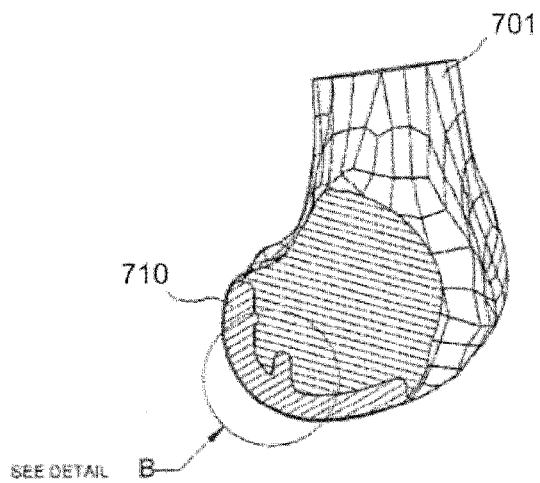
FIG. 51  FIG. 52

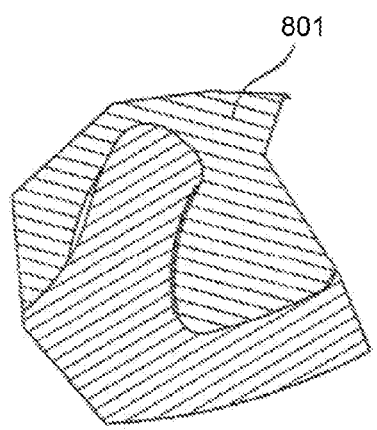
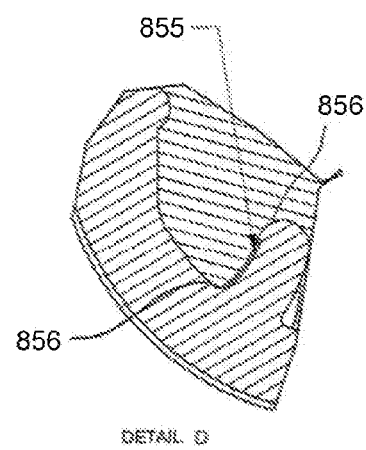
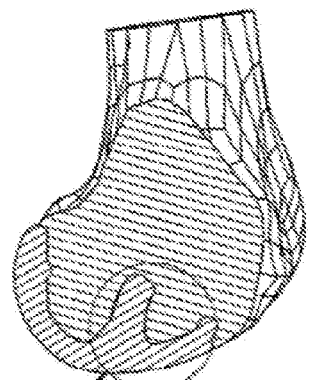
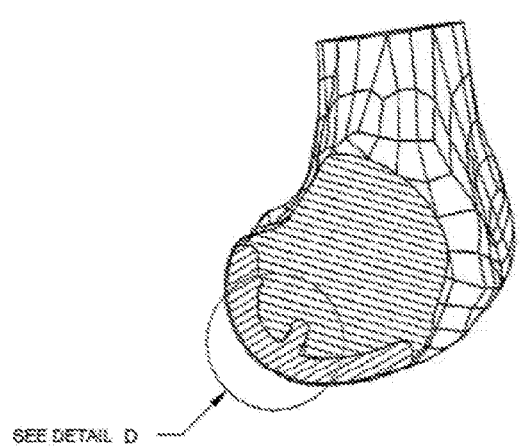
FIG. 55
FIG. 56

PROSTHETIC IMPLANT AND METHOD OF IMPLANTATION

CROSS-REFERENCE TO RELATED APPLICATIONS

The present application is a continuation of U.S. Patent Application Ser. No. 13/530,927, filed Jun. 22, 2012, which claims the benefit of the filing date of U.S. Provisional Patent Application No. 61/500,257 filed Jun. 23, 2011, the disclosures of which are both hereby incorporated herein by reference.

BACKGROUND OF THE INVENTION

In a traditional knee arthroplasty surgery, the diseased bone and/or cartilage of a patient is removed and replaced with a prosthetic implant. A surgeon typically prepares the bone using a hand-held oscillating saw blade or other cutting instrument guided by a resection guide or the like, which results in a series of planar bone surface resections. Additionally, the surgeon may use a drill, broach, tamp or other instrument to make holes, slots, depressions or the like in the bone. The planar bone resections and cylindrical bone holes are oriented to interface with flat surfaces and pegs and/or keels formed on a bone engaging surface of a prosthetic implant. An opposite side of the implant includes an articulation surface that is preferably designed to articulate with a like articulation surface formed on an implant to be implanted on the other bone of the knee.

Although implants designed to be implanted on planar cut surfaces of bones have been more widely utilized, implants meant to be implanted on non-planar surfaces have been designed and utilized in surgical procedures. The preparation methods for such implants are often very different than for the above-discussed traditional implants. For instance, milling devices are often utilized to prepare the bone surface to receive the implant. Again, these implants may employ pegs and/or keels to aid in the fixation of implant to the bone. Additionally, like in the traditional planar cut implants, cement or another fixation compound may be utilized to guarantee a solid connection between the implants and the bone.

One drawback in utilizing cements or the like is that the required cement layer often results in an unwanted transformation from a very precisely prepared surface to an imprecise prepared bone surface. This is largely due to the imprecise nature of working with cement. In a situation where a bone surface has been prepared to meet very specific dimensions, application of cement prior to implanting the implant will result in the surface exhibiting less than precise dimensions.

Therefore, there exists a need for implants that do not require the use of cement or the like, but yet remain attached to the bone after implantation.

BRIEF SUMMARY OF THE INVENTION

A first aspect of the present invention is a prosthetic implant including a first end, a second end, an articular surface, a bone contacting surface including a curved portion, a first element extending from the bone contacting surface and having a first curved surface and a second element extending from the bone contacting surface and having a second curved surface. The first and second curved surfaces are preferably curved about a first pivot point.

In other embodiments of this first aspect, the implant may further include a third element extending from the bone contacting surface and having a third curved surface, where the third curved surface is also curved about the first pivot point. The first and second curved surfaces may face the first end and the pivot point may be adjacent the first end. The implant may also include a third element extending from the bone contacting surface, the third element being located adjacent the second end. The third element may be at least partially arcuate.

In still further embodiments of the first aspect of the invention, the first element may further include a third curved surface and the second element further include a fourth curved surface, the third and fourth curved surfaces being curved about the first pivot point. The bone contacting surface may also include a flat portion defining a first plane, the first pivot point located along the first plane. In this construction, the first pivot point may be spaced apart from the first end. In another embodiment, the bone contacting surface may include a flat portion defining a first plane, the first pivot point located apart from the first plane. Again, the first pivot point may be spaced apart from the first end. In certain embodiment, the implant may be a femoral component, a tibial component, a patello-femoral component, or the like.

Another aspect of the present invention is another prosthetic implant including a first end, a second end, an articular surface, a bone contacting surface including a curved portion, a first element extending from the bone contacting surface and having a first curved surface and a second element extending from the bone contacting surface and having a second curved surface. The first curved surface may be curved about a first pivot point and the second curved surface may be curved about a second pivot point.

In another embodiment according to the second aspect, the implant includes a third element extending from the bone contacting surface and having a third curved surface, where the third curved surface is curved about one of the first or second pivot points. The first and second curved surfaces may face the first end and the first and second pivot points may be adjacent the first end. The implant may further include a third element extending from the bone contacting surface, the third element located adjacent the second end. The third element may be at least partially arcuate.

In other embodiments, the first element may further include a third curved surface and the second element may further include a fourth curved surface, the third curved surface being curved about the first pivot point and the fourth curved surface being curved about the second pivot point. The bone contacting surface may include a flat portion defining a first plane, the first and second pivot points located along the first plane. The first and second pivot points may be spaced apart from the first end. In other embodiments, the bone contacting surface may include a flat portion defining a first plane, the first and second pivot points located apart from the first plane. The first and second pivot points may be spaced apart from the first end. In the various embodiments, the implant may be a femoral component, a tibial component, a patello-femoral component or the like.

Yet another aspect of the present invention is a method of arthroplasty including the steps of creating a first resected bone surface on a first end of a bone, at least a portion of the first resected bone surface being non-planar, preparing a first cavity extending into the first resected bone surface, providing a prosthetic implant, the implant including an articular surface, a bone contacting surface including a curved portion and a first element extending from the bone contacting surface and having a first curved surface, the first curved surface curved about a first pivot point and coupling the implant by pivoting the implant about the first pivot point until the first element becomes disposed within the first cavity.

In an embodiment according to this aspect, the making step may include utilizing any suitable cutting instrument including, but not limited to, a miller, handheld cutting implement or a cutting tool coupled with a robot. The preparing step may further include preparing a second cavity extending into the first resected bone surface. The implant may include a second element extending from the bone contacting surface and having a second curved surface, the second curved surface curved about the first pivot point, and the implanting step may include disposing the second curved surface within the second cavity. Additionally, the implant may include a second element extending from the bone contacting surface and having a second curved surface, the second curved surface curved about a second pivot point, and the implanting step may include disposing the second curved surface within the second cavity. The first and second pivot points are at different locations.

In other embodiments, the first element may include a second curved surface. The preparing step may include preparing the first cavity to include a third curved surface corresponding to the first curved surface and a fourth curved surface corresponding to the second curved surface. The first, second, third and fourth surfaces may be curved about the first pivot point. The first and second surface may be curved about the first pivot point and the third and fourth surfaces may be curved about a second pivot point, the first and second pivot points being at different locations. The implant may further include a first projection facing a first end of the implant.

In still further embodiments, the method may further include the step of creating a first divot in the first resected surface. The implanting step may include disposing the first projection within the first divot. The method may further include the step of creating a second divot and the implanting step may further include disposing the first projection within the second divot. The first projection may be ball shaped, cylindrical or the like. The bone contacting surface may include a flat portion defining a first plane, the first pivot point located along the first plane or located apart from the first plane. The implanting step may be performed through the use of a robot or other suitable means.

Another aspect of the present invention is a prosthetic implant including an articular surface and a bone contacting surface. A first element extending from the bone contacting surface has a first center and a first radius. A second element extending from the bone contacting surface has a second radius and a third radius. The first radius, the second radius and the third radius are concentric about the first center.

In one embodiment of this aspect, the prosthetic implant may further comprise a third element that extends from the bone contacting surface and has a fourth radius. The fourth radius being concentric about the first center.

Another aspect of the present invention is a method of bone preparation and insertion of a unicondylar prosthetic implant. The method may include utilizing any suitable cutting instrument including, but not limited to, a miller, handheld cutting implement or a cutting instrument coupled to a robot or the like to make a non-planar resection on a distal femoral bone and using the robot/cutting instrument construct to prepare a first cavity and a second cavity extending into the bone. The method further includes implanting a unicondylar implant by following an implantation path having a first center that follows an approach path until a first element thereof contacts the first cavity, and then follows a substantially curved path until the first element is fully seated in the first cavity and a second element is fully seated in the second cavity.

In one embodiment of this aspect, the unicondylar implant may be implanted through the use of a robot or the like.

In another embodiment of this aspect, the second cavity has an anterior aspect and a posterior aspect, and the second element further includes an anterior surface and a posterior surface, wherein the anterior surface has an interference fit with the anterior aspect of the second cavity and at least a portion of the posterior surface has a clearance fit with the posterior aspect of the second cavity.

Another aspect of the present invention is a system for surgery. The system includes a prosthetic implant having an articular surface and a first element, the first element having a first center. The system may further include any suitable cutting instrument including, but not limited to, a miller, handheld cutting implement or a bone preparation system coupled with a robot or the like for preparing a non-planar geometry and a robot or the like for inserting the prosthetic implant into the non-planar geometry. The system may further include an implantation path programmed into the robotic, wherein the first center is coincident along the implantation path during implantation.

In one embodiment of this aspect, the implantation path follows a first linear path until the first element contacts the bone, and then follows a second curved path until the prosthetic implant is fully seated into the prepared bone.

In another embodiment of this aspect, the prosthetic implant has a second element which has a first surface having a geometry that is concentric about the first center.

In yet another embodiment of this aspect, the prosthetic implant rotates about the first center while the first center remains coincident about the implantation path while moving along the implantation path. The concentric geometries form a concentric path about the first center during rotation.

BRIEF DESCRIPTION OF THE DRAWINGS

The present invention will be better understood on reading the following detailed description of non-limiting embodiments thereof, and on examining the accompanying drawings, in which:

FIGS. 40a-40d are a series of cross-sectional views illustrating a method of implantation for the implant shown in FIG. 37.

FIG. 51 is a partial cross sectional view of the implant of FIG. 49 implanted on a femur.

FIG. 52 is another partial cross sectional view of the implant of FIG. 49 implanted on a femur.

FIG. 55 is a partial cross sectional view of the implant of FIG. 53 implanted on a femur.

FIG. 56 is another partial cross sectional view of the implant of FIG. 54 implanted on a femur.

DETAILED DESCRIPTION

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

The present invention addresses the aforementioned shortcomings with certain of the prior art implants. Specifically, the present invention provides implants that can be implanted with or without the use of cement or other adhesive, but remain attached to the bone even in instances where no cement or other adhesive is utilized. Although discussed below primarily in connection with knee arthroplasty procedures, it should be noted that implants according to the present invention can be modified for use in other joints throughout the body. For instance, while the main aim of the implants shown and described in the present application relate to implants for the distal femoral surface and the proximal tibial surface, implants according to the present invention could be utilized in the shoulder, spine, hip, patella or the like. In addition, although the present implants are designed to be implanted without the use of cement or the like, it should be understood that such compounds could be utilized to further ensure proper attachment of the implants to the bone.

Figure 1:
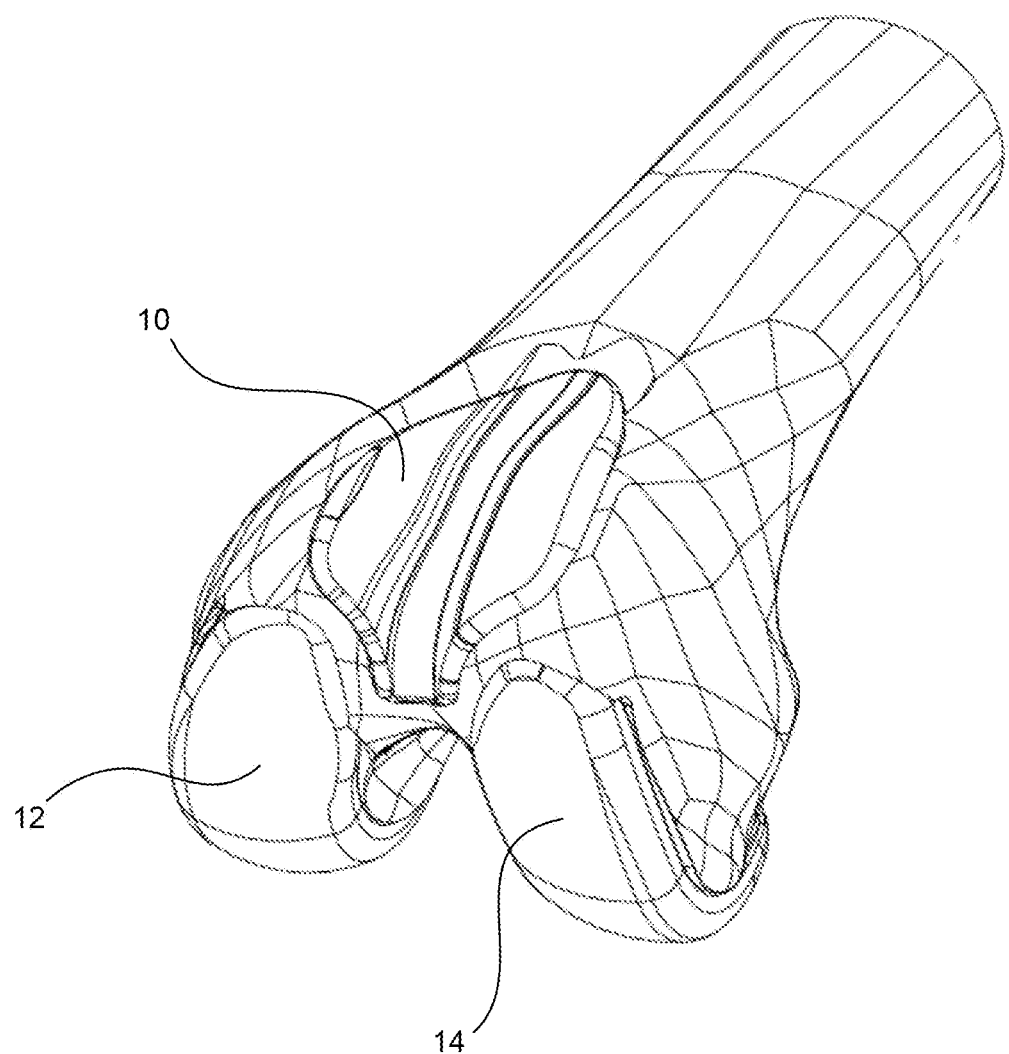
FIG. 1 is a perspective view of an implanted three part implant system according to one embodiment of the present invention.
Figure 2:
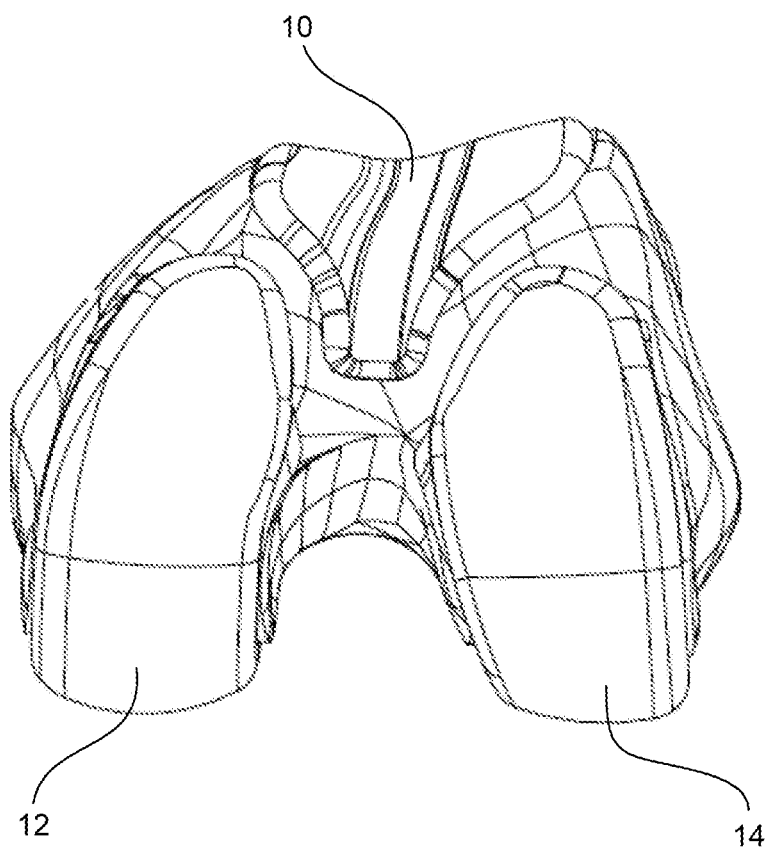
FIG. 2 is another perspective view of the implanted three part implant shown in FIG. 1.
Figure 3:
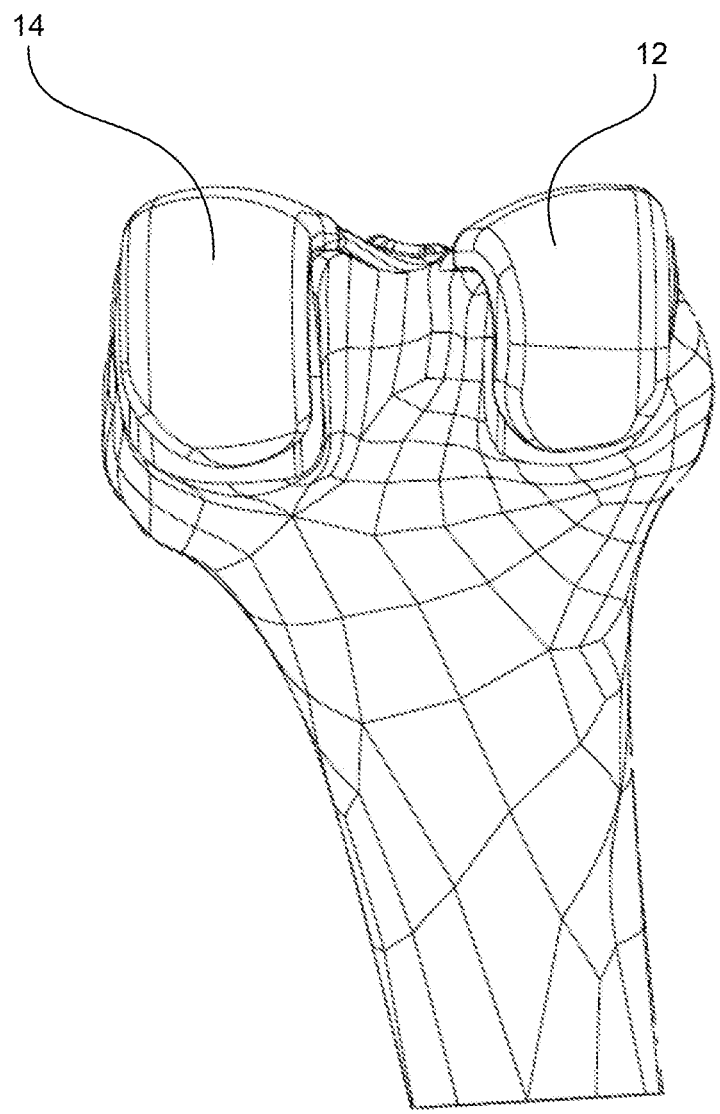
FIG. 3 is yet another perspective view of the implanted three part implant shown in FIG. 1.
Figure 4:
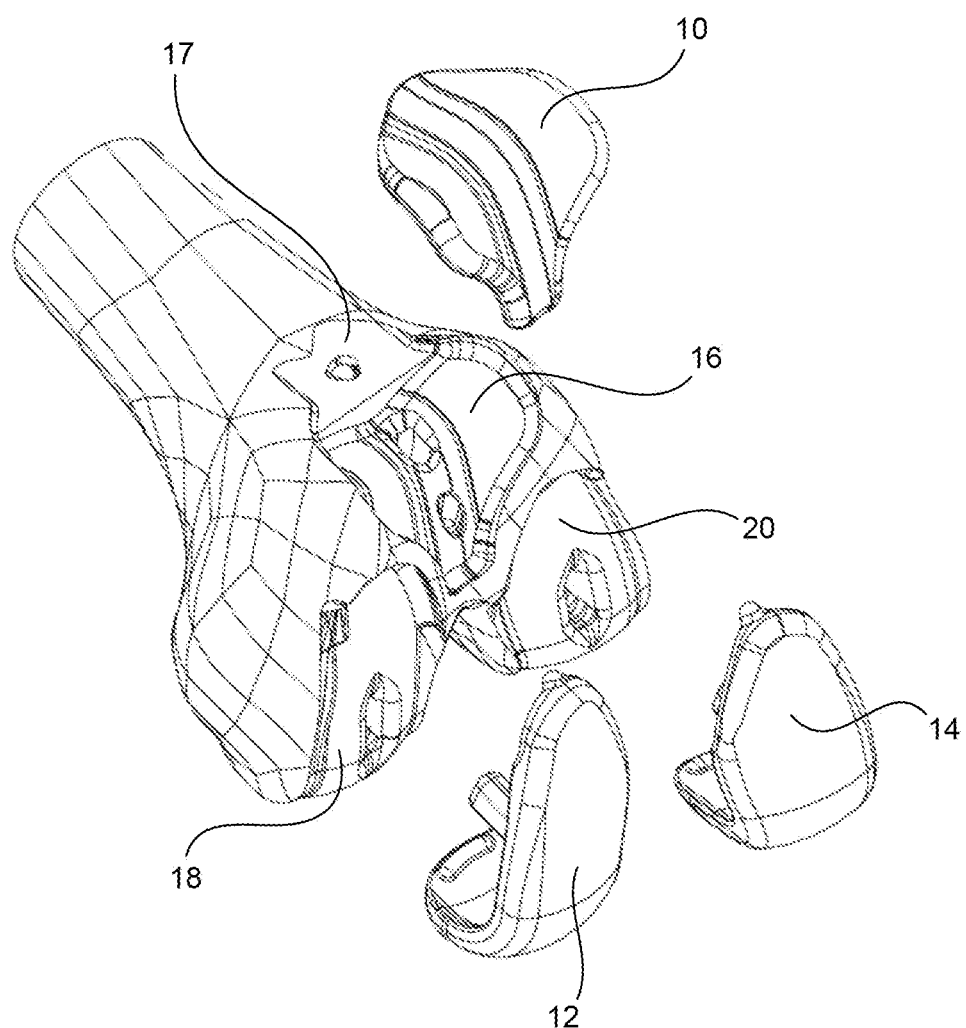
FIG. 4 is an exploded view of the three part implant shown in FIG. 1.
Figure 5:
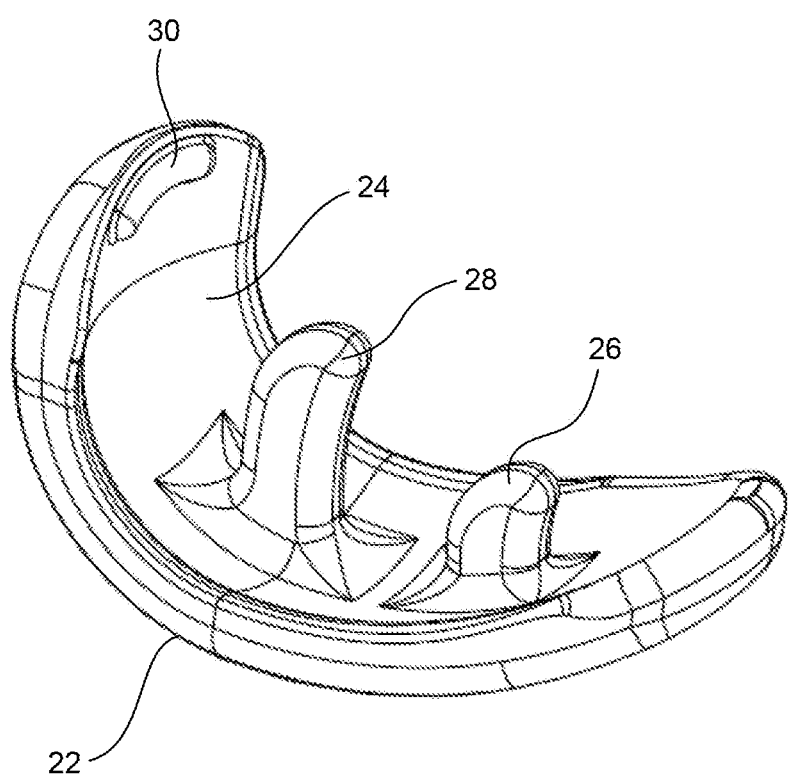
FIG. 5 is a perspective view of a femoral condyle implant of the three part implant shown in FIG. 1.
Figure 6:
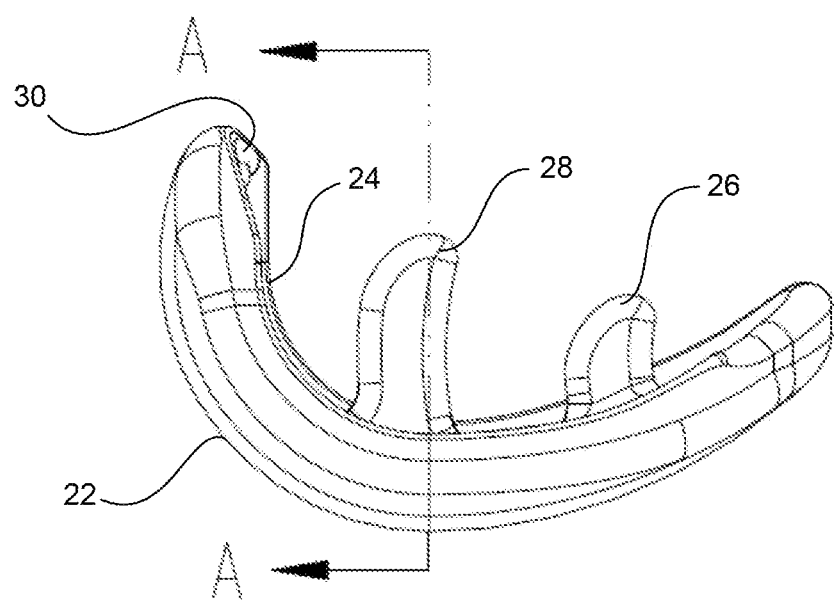
FIG. 6 is a side view of the femoral condyle implant shown in FIG. 5.
Figure 7:
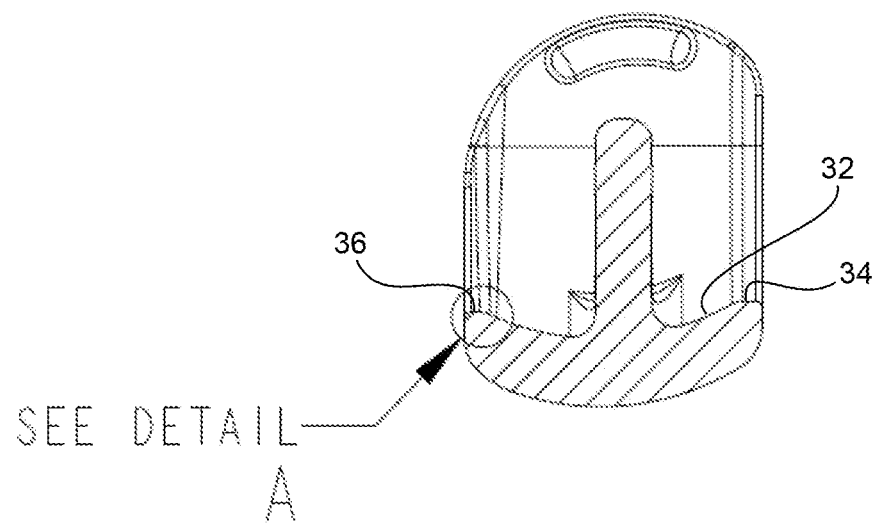
FIG. 7 is a cross sectional view the taken along line A-A of FIG. 6.
Figure 8:
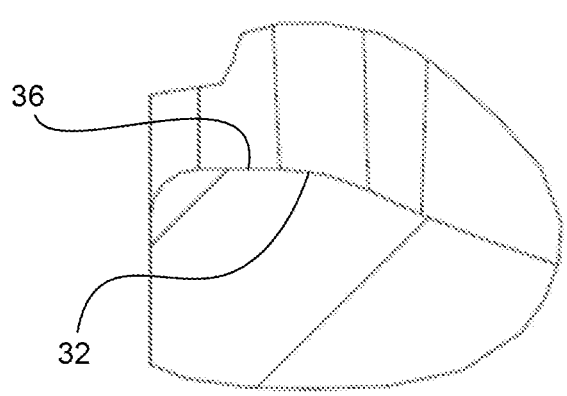
FIG. 8 is an enlarged view of area A of FIG. 7.
Figure 9:
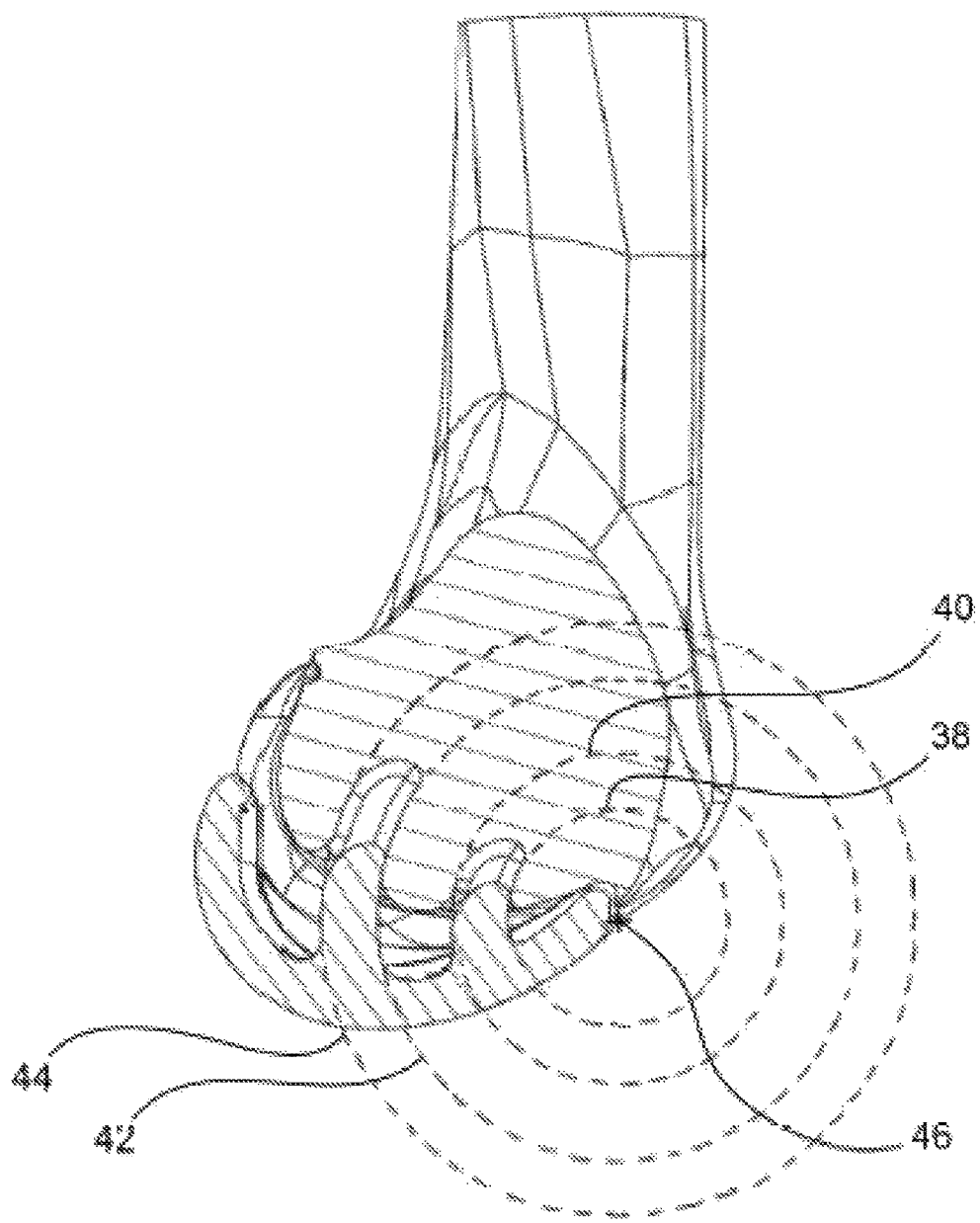
FIG. 9 is a partial cross sectional view of the implant of FIG. 5 and its relationship with a prepared tibia.
Figure 10C:
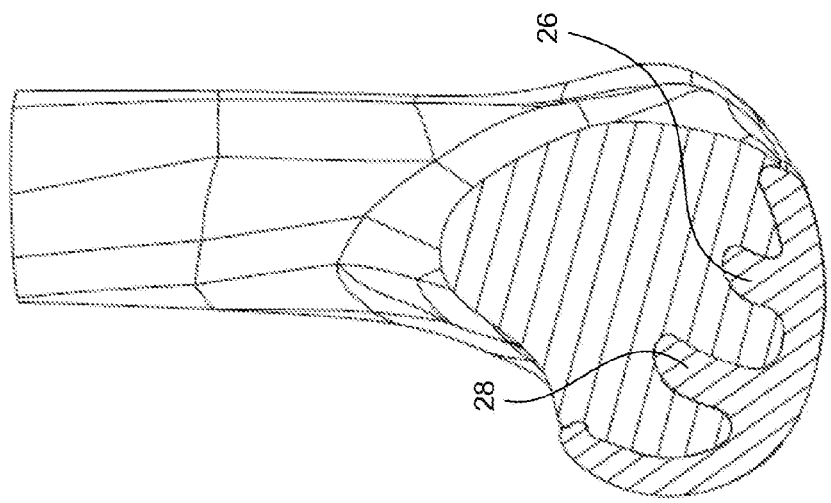
FIGS. 10A-10C are partial cross sectional view of the implant of FIG. 5 being implanted on a prepared femur.
Figure 10B:
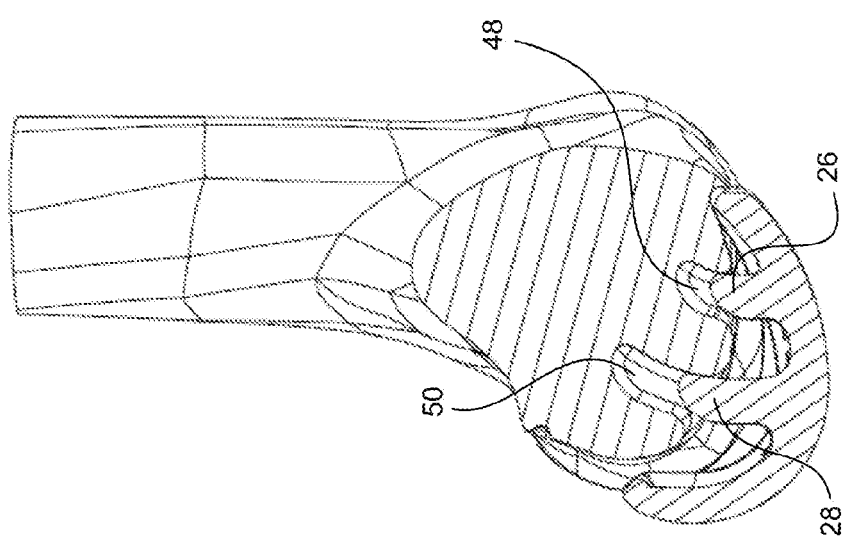
Figure 10A:
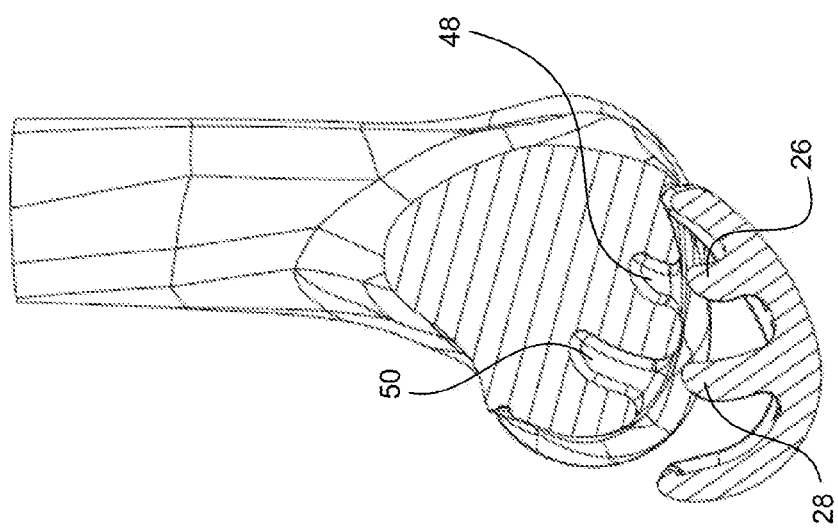

Turning now to the various embodiments of the present invention, FIGS. 1-4 depict a three-part implant system including a patello-femoral implant 10, a medial femoral condyle implant 12, and a lateral femoral condyle implant 14. As is apparent from the exploded view of FIG. 4, those three implants are designed for implantation both within recesses and on flat cuts formed in the distal end of the femur. This type of design will be referred to herein as an inlay/onlay construction. For instance, patello-femoral implant 10 is implanted in a patello-femoral recess 16 and on a patella-femoral flat 17, medial femoral condyle implant 12 is implanted in a medial condyle recess 18, and lateral condyle implant 14 is implanted in a lateral condyle recess 20. Recesses 18 and 20 may in fact include portions that when viewed from a specific orientation appear flat. For instance, FIGS. 9-10C depict a posterior portion of one of the recessed that appears flat in the particular views shown. However, it is to be understood that, when viewed from different orientations (e.g., from an orientation rotated ninety degrees from that shown in FIGS. 9-10C), those "flat" portions may in fact exhibit a curvature. Moreover, it is to be understood that recesses 18 and 20 may include portions that are surrounded by unresected (e.g., on the anterior end of the condyles) and other portions that are not surrounded (e.g., on the posterior end of the condyles). As is best shown in FIG. 1, the cooperation of the implants and the prepared bone creates an articulation surface on the distal end of the femur that consists of both the implants and the natural femoral cartilage (i.e., the cartilage extending between the prepared surfaces). Of course, implants 10, 12, 14 may be designed to cooperate with a distal end of the femur that is completely prepared, not just prepared within the aforementioned recesses.

Turning now to FIGS. 5-8, the general design of certain of the common features between femoral condyle implants 12 and 14 will be described. It should be noted that in certain embodiments, the construction of these common features of femoral condyle implants 12 and 14 are substantially similar, but may vary in other embodiments. Moreover, other aspects of femoral condyle implants 12 and 14 may vary significantly in order to ensure the cooperation of the particular implant with the different anatomical features of the lateral and medial femoral condyles. As shown, both implants 12 and 14 include an articulation surface 22 and a bone engaging surface 24. Articulation surface 22 may be of any shape designed to cooperate with a corresponding articulation surface formed on a tibial implant, such as the tibial implants discussed below. In this regard, it should be understood that articulation surface 22 may vary greatly depending upon the overall construction of the other components of the system. For instance, the articulation surfaces described in U.S. Pat. Nos. 7,160,330 and 7,628,817, the disclosures of which are hereby incorporated by reference herein, may be employed in the implant designs. Bone engaging surface 24 is generally curvate, although it may be only partially curvate in other embodiments, with three components extending therefrom, a first peg 26, a second peg 28, and a snap feature 30. It should be understood that although specific structures such as pegs 26 and 28 and snap feature 30 are depicted in the drawings and described herein, other structures are indeed contemplated, including the use of keels, spikes and the like. With respect to its curvature, bone engaging surface 24 is curved both in an anterior to posterior direction (see FIGS. 5 and 6) and in a medial to lateral direction denoted by curvature 32 (see FIGS. 7 and 8). Moreover, surface 24 includes lateral and medial flat run outs 34 and 36 (best shown in FIGS. 7 and 8). In essence, run outs 34 and 36 allow for a smooth transition between the implant and the bone surrounding the recesses into which the implants are placed, while ensuring implant stability. In a similar fashion to the above-discussed recessed which are formed in the bone, run outs 34 and 36 are preferably only flat when viewed from the particular orientation depicted in FIGS. 7 and 8. However, when viewed from an orthogonal orientation, the run outs may in fact be curved. In the particular configuration shown, the orientation of the flat run outs is substantially perpendicular to the planned loading direction of the implant to ensure maximum stability. In addition, the run outs serve as a termination of the bone contacting surface, which in turn, determines the amount of bone that needs to be prepared for accepting the implant.

As best shown in FIG. 9, first and second pegs 26, 28 are situated in a manner that facilitates a snap, press or interference fit with the bone. It should be recognized that these fits may be facilitated in various ways, including through line-to-line cooperation between and among the various implant components (e.g., pegs 26, 28) and the prepared bone. Moreover, as will be discussed more fully below, the particular orientation of the implant components and/or the prepared surfaces of the bone may create the given fit. More specifically, first peg 26 includes an anteriorly facing surface at least a portion of which is curved along a first imaginary circle 38, and a posterior facing surface at least a portion of which is curved along a second imaginary circle 40. Likewise, an anterior facing surface of second peg 28 is curved along a third imaginary circle 42, and a posterior facing surface of that peg is curved about a fourth imaginary circle 44. As is depicted in FIG. 9, each of those four circles is centered about a center point 46, which in the embodiment disclosed in FIG. 9 serves as a pivot point for the implant (as will be discussed more fully below). Center/pivot point 46 happens to be adjacent an anterior surface of the implant in the embodiment shown, however, it should be understood that such point could be located away from the implant or at various location on the implant.

In a preferred method of implanting the embodiment implant shown, the distal end of the femur is prepared so as to include an overall profile complementary to that of bone facing surface 24 and first and second holes 48 and 50 for receiving pegs 26 and 28, respectively. Hole 48 includes a posteriorly facing surface at least a portion of which is curved along circle 38 and an anteriorly facing surface at least a portion of which is curved along circle 40, while hole 50 includes a posteriorly facing surface at least a portion of which is curved along circle 42 and an anteriorly facing surface at least a portion of which is curved along circle 44. Additionally, as will be discussed more fully below in connection with the discussion of FIG. 11, the bone is preferably prepared so that the anterior portion of the implant can be first engaged with the prepared bone (FIG. 10A) and then the remainder of the implant can be pivoted into position so that first and second pegs 26 and 28 are disposed within first and second holes 48 and 50, respectively (FIG. 10B) and the implant is ultimately snap or press fit onto the distal portion of the bone (FIG. 10C). As best shown in FIG. 10C, holes 48 and 50 are sized to create an interference fit with pegs 26, 28, respectively, so that the pegs are ultimately tightly fit therein. Of course, in other embodiments, the holes may be created larger than the pegs.

It should be understood that although holes 28 and 50 are shown and described as being formed in the bone, such structures may vary depending upon the particular configuration of the implants.

Figure 11:
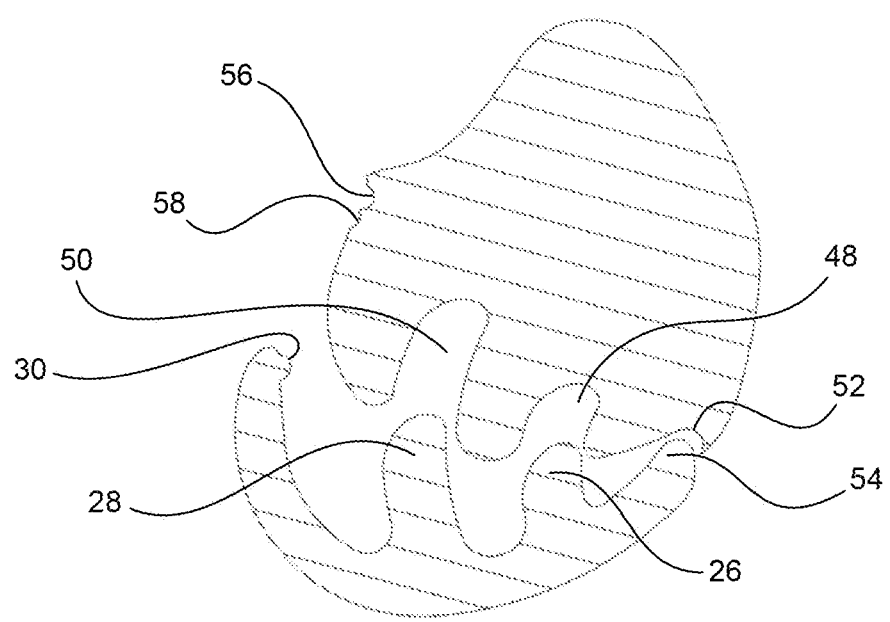
FIG. 11 is an enlarged cross sectional view depicting the relationship shown in FIG. 9.
Figure 12:
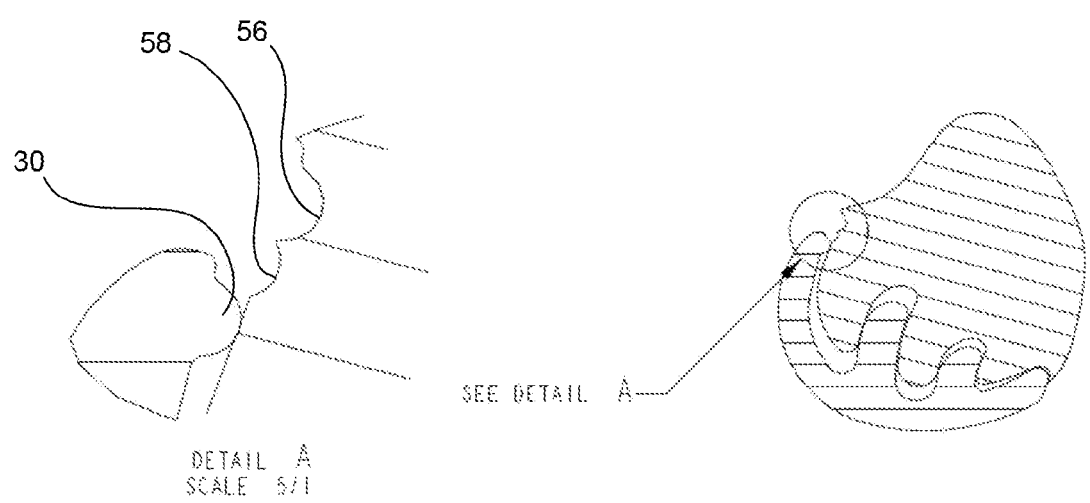
FIG. 12-14 are enlarged views focusing on a portion of the relationship shown in FIG. 11.
Figure 13:
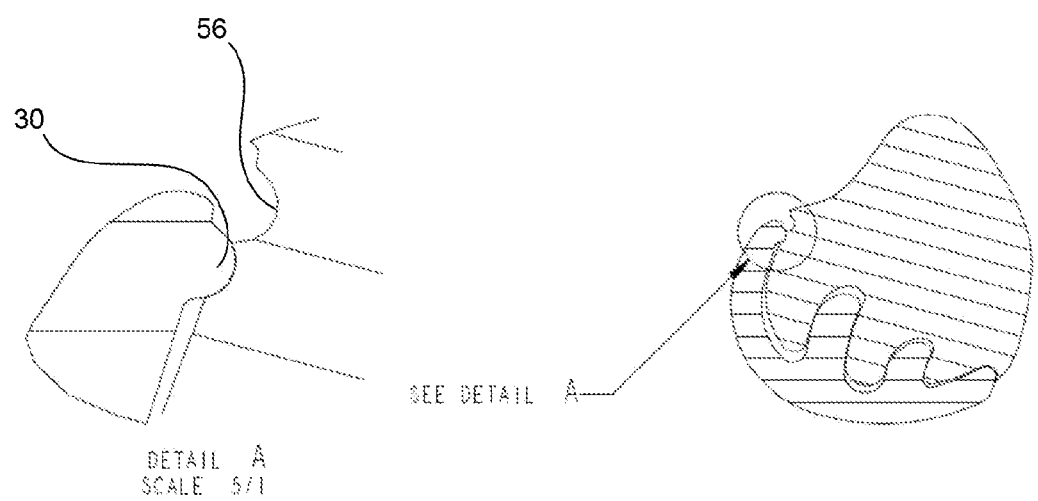
Figure 14:
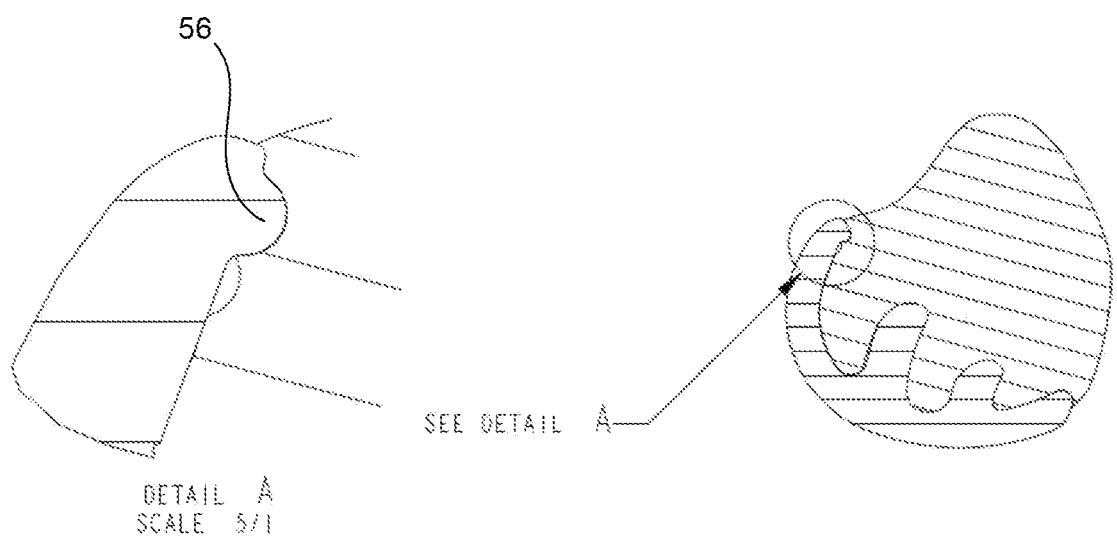

The aforementioned implantation of the implant with the distal portion of the femur is possible because of the relationship of pegs 26 and 28 and the specially prepared femoral surface. In particular, holes 48 and 50 are situated and similarly curved so as to receive the pegs when the implant is pivoted about center point 46. As shown in FIG. 11, the distal portion of the femur is also prepared so as to include a pivot surface 52 that cooperates with the anterior of the implant. In this regard, it is noted that the implant preferably includes a curved anterior surface 54 to facilitate the pivoting. In other embodiments, the implant may include a separate structure, such as a bulbous extension that allows for the pivoting (shown in certain embodiments discussed below). In still further embodiments, the implant may be pivoted about a virtual pivot rather than a specific structure. A posterior portion of the femur is also preferably prepared to include at least one divot 56 for accepting snap feature 30. This cooperation, as best shown in FIG. 14, provides an additional fixation to the implant and bone construction. In the particular configuration shown in FIG. 11, a secondary divot 50*a* is also created so as to allow an easy transition of snap feature 30 into divot 56. The progression of snap feature 30 into the two divots is best shown in FIGS. 12-14. Secondary divot 58 essentially provides a first relief, thereby allowing snap feature 30 to smoothly transition into divot 56. In other words, the cooperation occurs in a stepwise fashion, which is important because either the implant or the bone needs to deflect somewhat to allow for snap feature 30 to become seated within divet 56. Secondary divet 58 provides for less deflection of both the bone and implant, which necessarily reduces the possibility of implant deformation and/or fracture of the bone.

Figure 15:
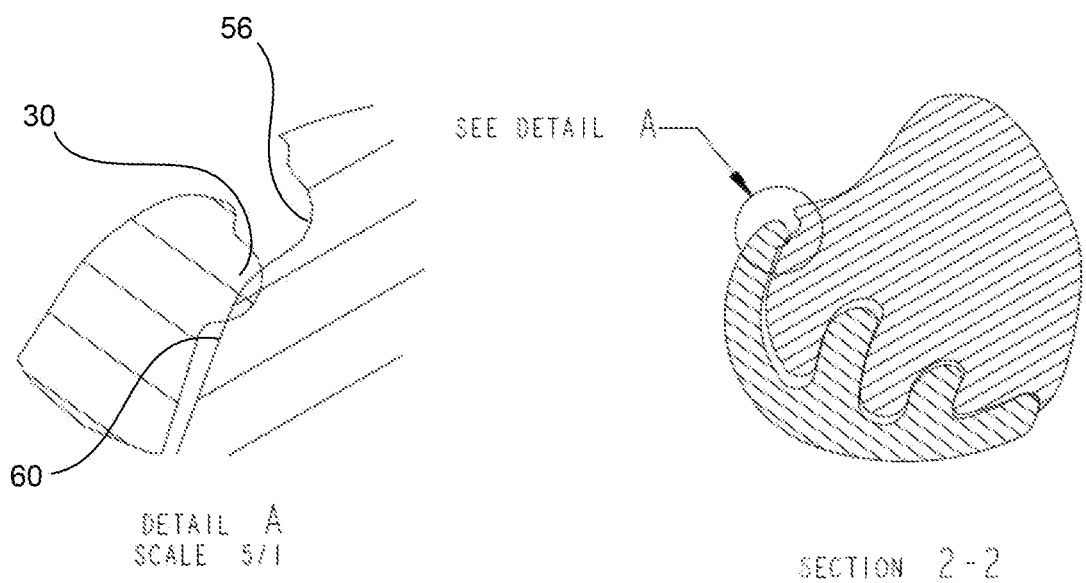
FIGS. 15-16 are enlarged views similar to those of FIGS. 12-14 depicting an alternately prepared bone.
Figure 16:
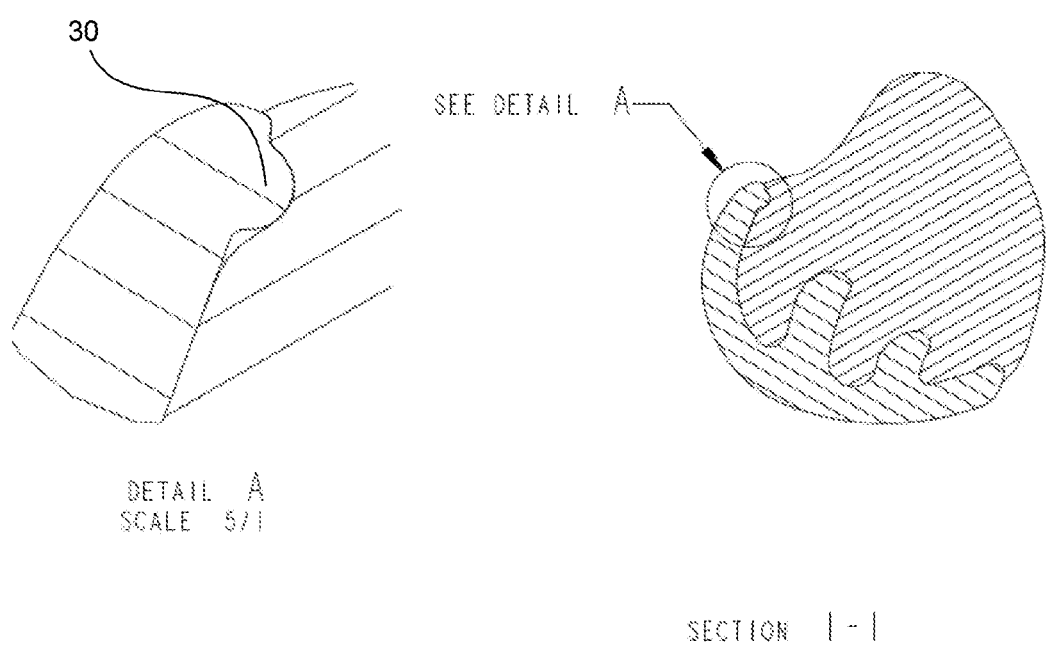

FIGS. 15 and 16 depict a similar progression of snap feature 30 into divot 56, without the inclusion of a secondary divet 58. In the embodiment shown in those figures, the bone is prepared so that it includes a tapered surface 60 that acts essentially as an infinitely stepped surface. Thus, divot 56 can move along surface 60 and into divot 56 without requiring significant deformation of the implant and/or causing fracture of the bone. Essentially, in both the embodiment shown in FIGS. 12-14 and the embodiment shown in FIGS. 15 and 16, a transition is created to prevent the deformation of the implant and/or fracture of the bone. In other embodiments, such transition may take on various geometries.

Figure 17:
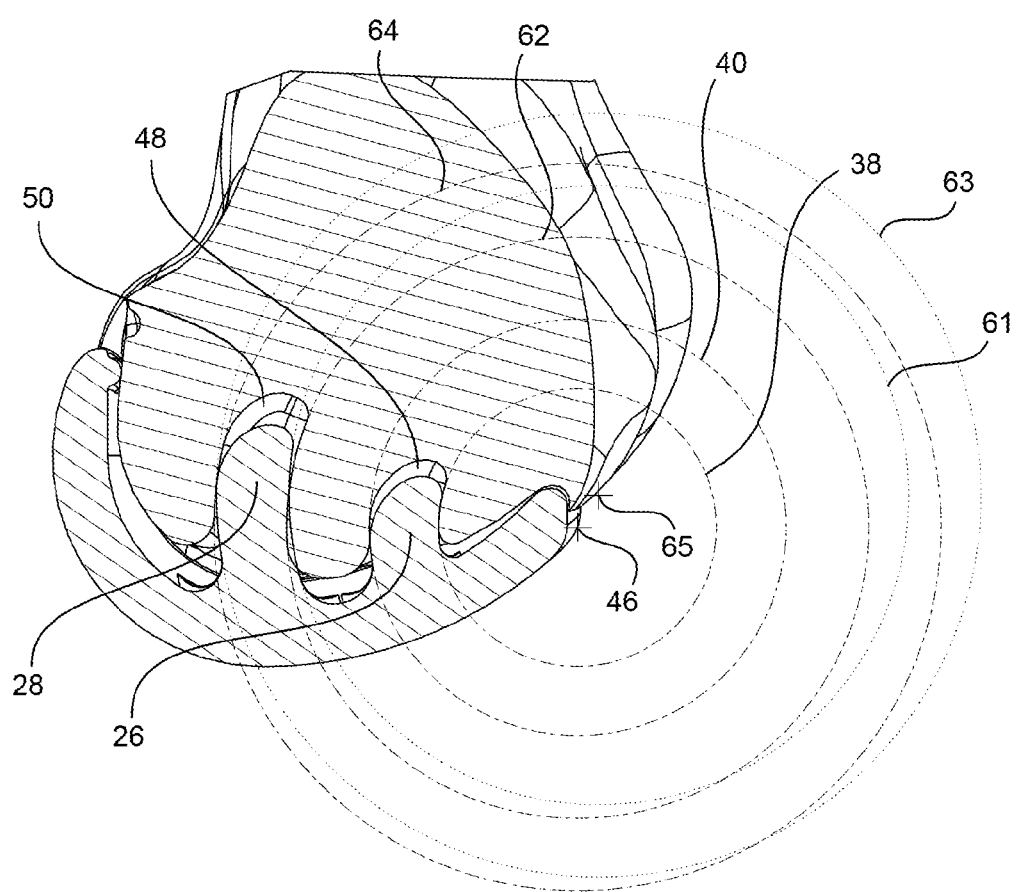
FIG. 17 is a partial cross sectional view similar to FIG. 9 depicting an alternately prepared bone.
Figure 18:
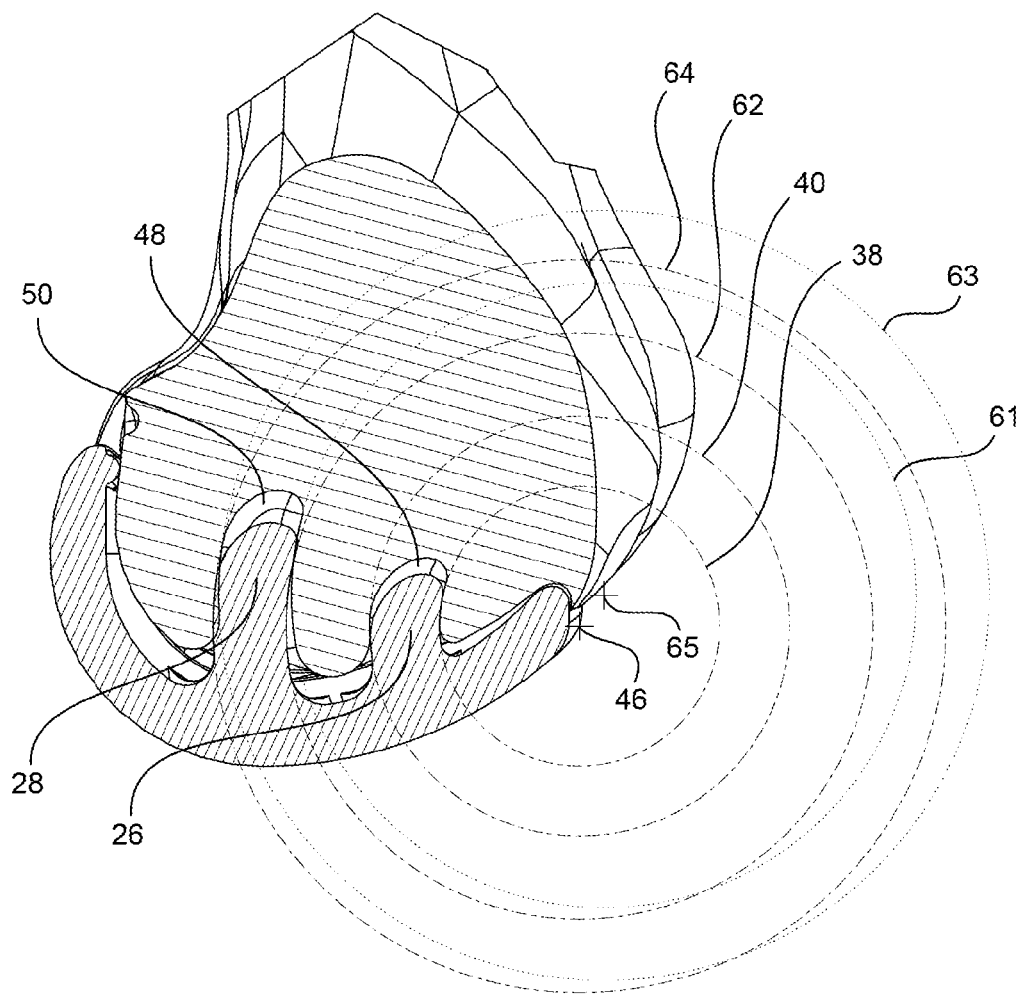
FIG. 18 is an enlarged cross sectional view similar to FIG. 11 depicting the alternate bone preparation shown in FIG. 17.

FIGS. 17 and 18 illustrate alternate embodiments for the cooperation between the implant and the prepared distal portion of the femur. In FIG. 17, first peg 26 includes remains concentric with first hole 48, as in the embodiment shown in FIG. 9, but peg 28 is situated differently. Specifically, peg 26 includes an anteriorly facing surface and hole 48 includes a posteriorly facing surface, both of which include portions that are curved along a first imaginary circle 38, and peg 26 includes a posterior facing surface and hole 48 includes an anteriorly facing surface, both of which include portions that are curved along a second imaginary circle 40. Both circles 38 and 40 are curved about center point 46. Moreover, hole 50 includes a posteriorly facing surface at least a portion of which is curved along a third imaginary circle 62 and an anteriorly facing surface at least a portion of which is curved along a fourth imaginary circle 64. Again, both circles 62 and 64 are curved about center point 46. However, peg 28 includes an anteriorly facing surface at least a portion of which is curved along a fifth imaginary circle 61 and a posteriorly facing surface at least a portion of which is curved along a sixth imaginary circle 63. Both circles 61 and 63 are curved about a center point 65, which is different from center point 46.

On the other hand, FIG. 18 depicts a situation where the implant remains in same form as it is shown in FIG. 9 (i.e., pegs 26 and 28 include surfaces a portion of which are curved along concentric circles), but where hole 50 includes surfaces having a portion curved along non-concentric circles. Specifically, the relationship depicted in FIG. 17 between peg 26 and hole 48 remains the same. Peg 28 includes an anteriorly facing surface a portion of which is curved along imaginary circle 62 and a posteriorly facing surface a portion of which is curved along imaginary circle 64, where both of those circles are curved about center point 46. However, hole 50 includes a posteriorly facing surface a portion of which is curved along imaginary circle 61 and an anteriorly facing surface a portion of which is curved along imaginary circle 63. Those circles 61, 63 are curved about center point 65, which is different than center point 46.

Figure 19:
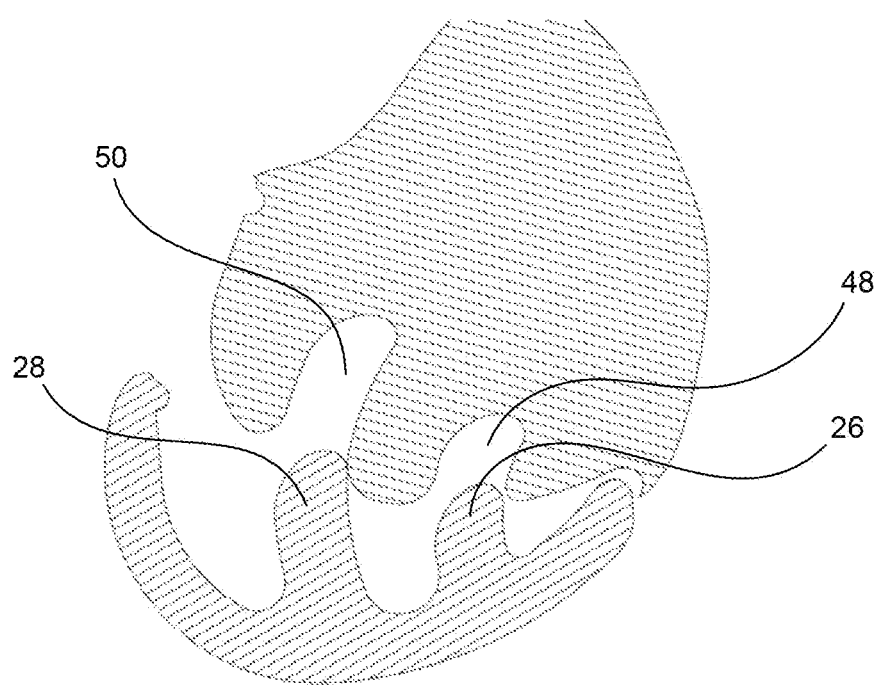
FIGS. 19 and 20 are partial cross sectional views similar to FIGS. 10A-10C depicting the alternate bone preparation shown in FIG. 17.
Figure 20:
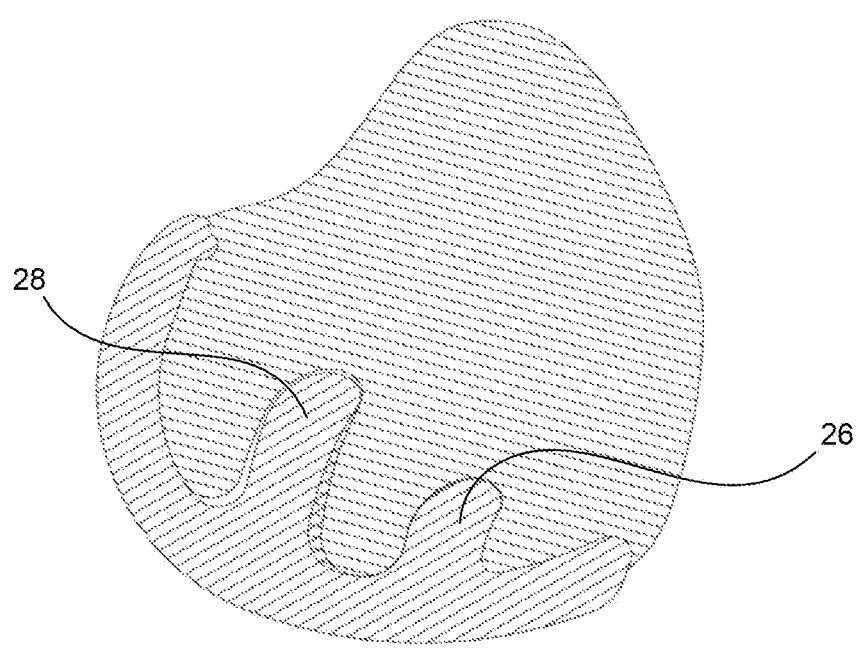
Figure 21:
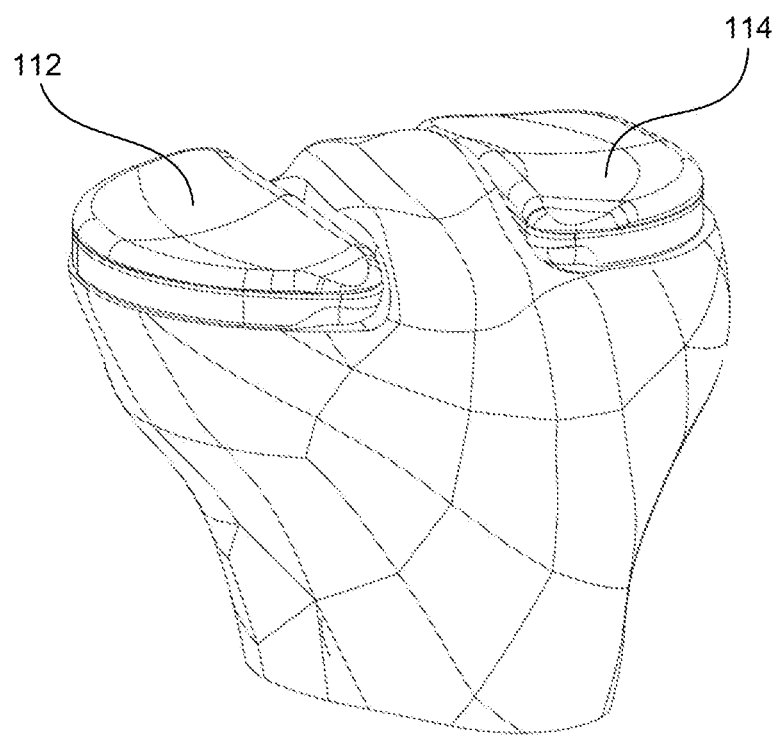
FIG. 21 is a perspective view of implanted tibial implants in accordance with the present invention.

In both FIGS. 17 and 18, the non-concentric relationship between peg 28 and hole 50 creates an interference fit when the peg is ultimately disposed within the hole. FIGS. 19 and 20 depict the representative progression of implantation of an implant into a prepared bone in accordance with that shown in FIGS. 17 and 18. While FIGS. 17 and 18 depict two different manners in which the non-concentric relationship can be created to result in an interference fit, others exist. For instance, instead of an interference fit being formed between peg 28 and hole 50, an interference fit can be created between peg 26 and hole 48 by varying their relationship in much of the same way as is described above in connect with FIGS. 17 and 18. In addition, it is contemplated to create an implant and bone relationship where interference fits exist between multiple pegs and multiple holes. For instance, both pegs 26 and 28 may exhibit a non-concentric relationship with holes 48 and 50. In other embodiments, implants having more than two pegs or other fixation members may likewise include multiple or only one non-concentric relationship.

Figure 22:
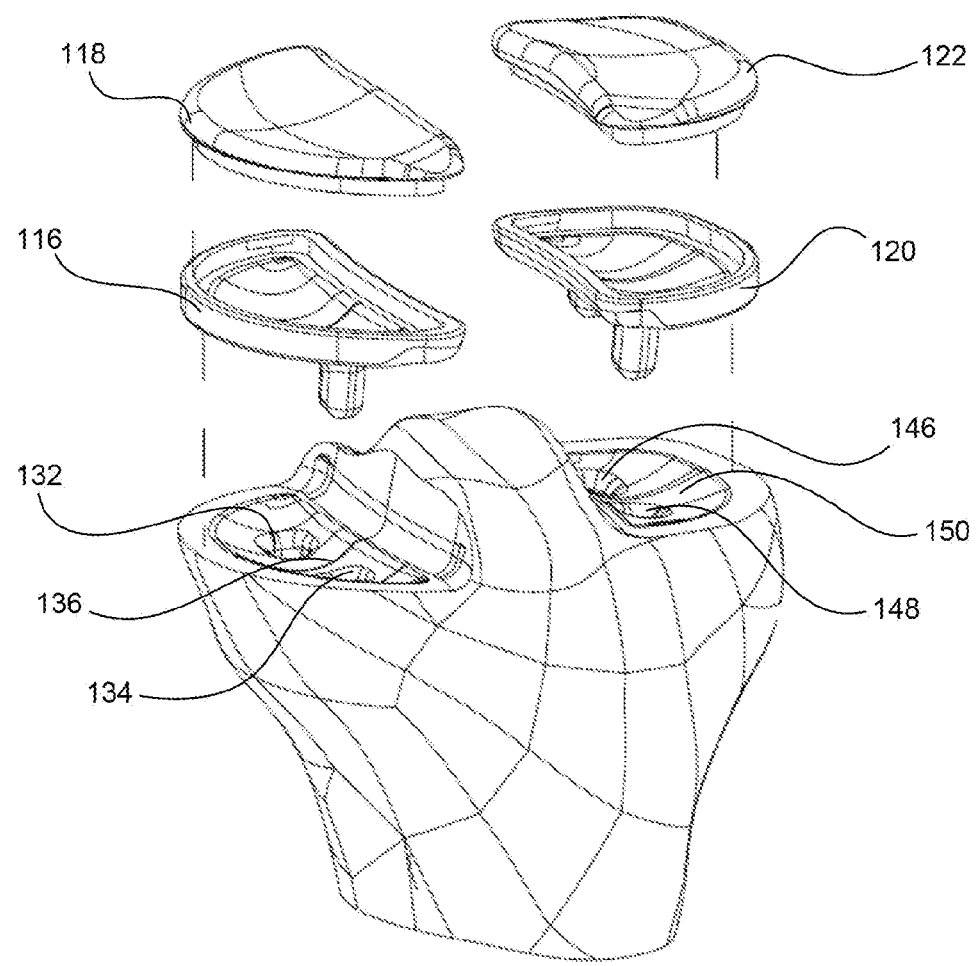
FIG. 22 is an explode view of the tibial implants shown in FIG. 21.
Figure 23:
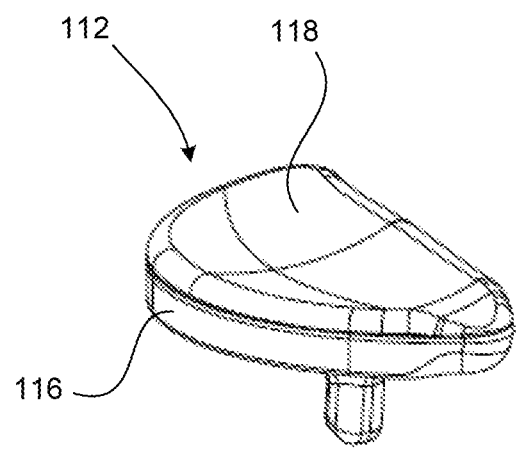
FIG. 23 is a perspective view of the lateral tibial implant shown in FIG. 21.
Figure 24:
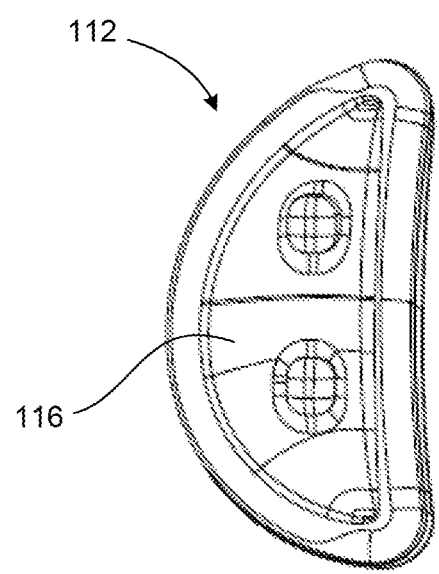
FIG. 24 is a bottom view of the lateral tibial implant shown in FIG. 21.
Figure 25:
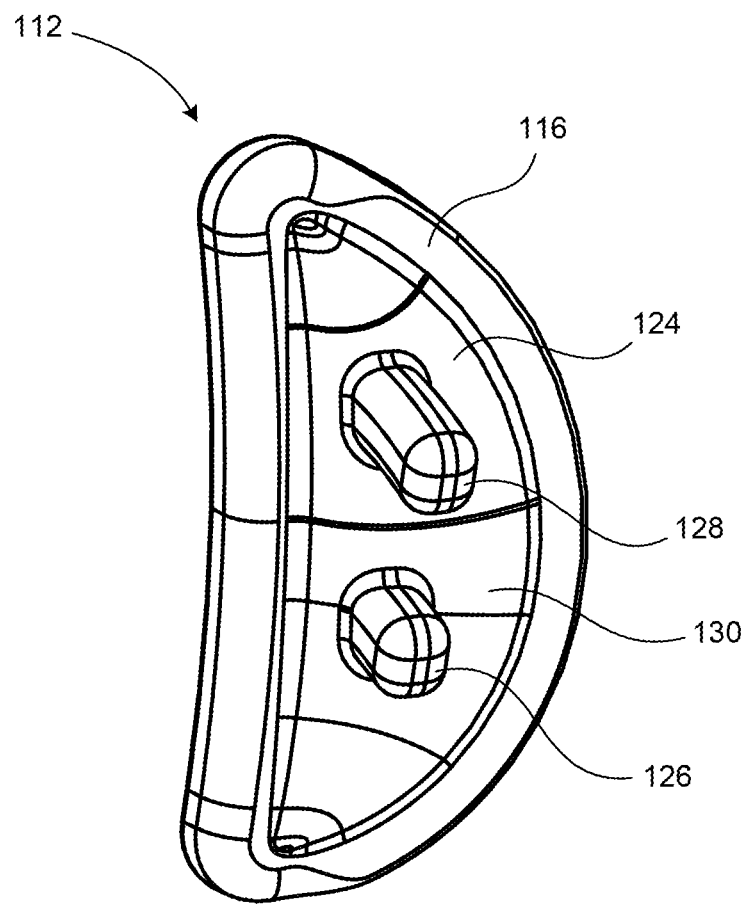
FIG. 25 is another perspective view of the lateral tibial implant shown in FIG. 21.
Figure 26:
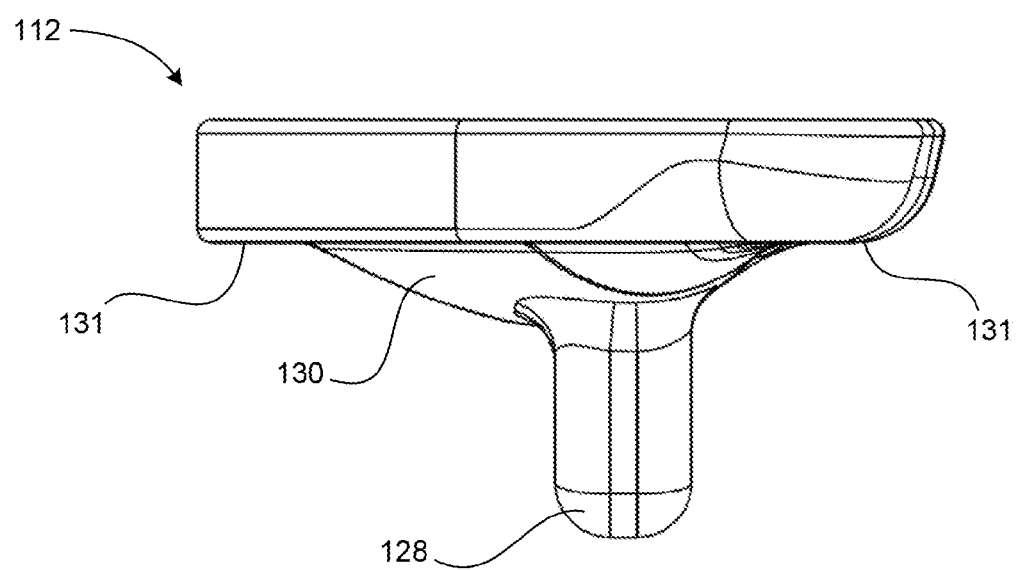
FIG. 26 is a front view of the lateral tibial implant shown in FIG. 25.
Figure 27:
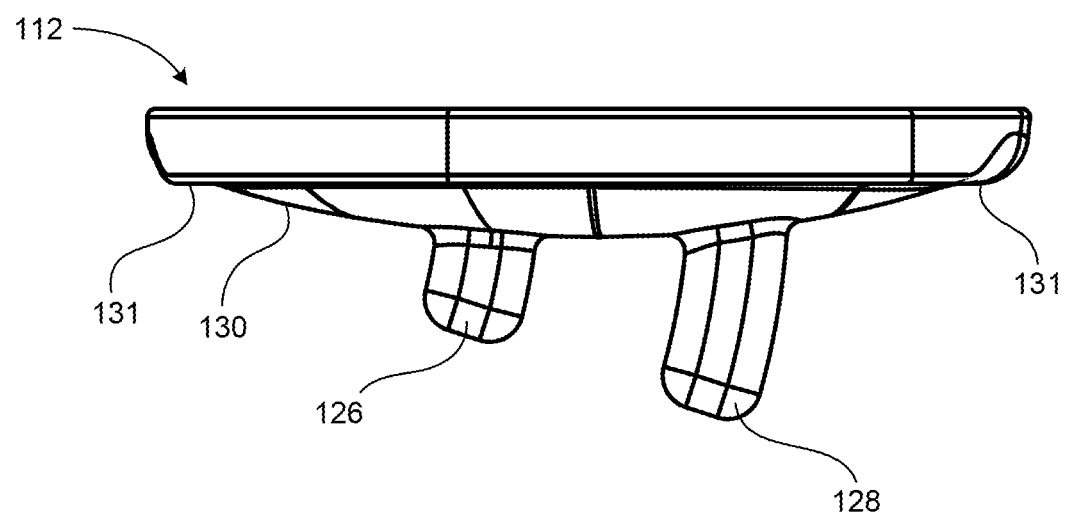
FIG. 27 is a side view of the lateral tibial implant shown in FIG. 25.

FIGS. 21-33 depict another embodiment according to the present invention, this embodiment pertaining to implants for use in replacing a proximal portion of the tibia. Specifically, tibial implants 112 and 114, corresponding to the medial and lateral sides of the tibia, respectively, are shown and described in those figures. As best shown in the exploded view of FIG. 22, medial implant 112 includes a medial baseplate 116 and a medial insert 118, while lateral implant 114 includes a lateral baseplate 120 and a lateral insert 122. In the preferred embodiment, the base plates are constructed of a metallic material, such as titanium, while the inserts are constructed of a polymer material, such as the crosslinked polyethylene offered under the name X3® by Stryker Corporation. Of course, other embodiments may include base plates and inserts formed of various other materials, the only limitation really being that such materials must be biologically acceptable. Likewise, although not focused upon in any of the figures, it should be understood that implants 112 and 114 employ structures for causing their inserts to be fixed to their baseplates. These structures can be any known or hereafter developed structures.

Turning now to FIGS. 23-27, the general design of certain of the common features between tibial implants 112 and 114 will be described in the context of a discussion of implant 112. It should be noted that in certain embodiments, the construction of these common features are substantially similar, but may vary in other embodiments. Moreover, other aspects of the tibial implants 112 and 114 may vary significantly in order to ensure the cooperation of the particular implant with the different anatomical features of the tibia. With a focus on medial tibial implant 112, it is shown that baseplate 116 has a bone facing surface 124 that itself includes first and second pegs 126 and 128, a domed underside surface 130 (best shown in FIGS. 26 and 27), and a flat run out 131 extending around domed surface 130. Referring back to FIG. 22, it is noted that the proximal portion of the tibia is preferably prepared in such fashion to receive pegs 126, 128, domed surface 130 and run out 131. In this regard, the tibia is preferably prepared to include holes 132, 146 and 134, 148 as well as a curved profile 136, 150, respectively. It should be understood that although both tibial implants 112 and 114 are shown as having domed underside surfaces, their respective bone facing surfaces may simply be flat, or even of a different configuration, such as concave surfaces.

Figure 28:
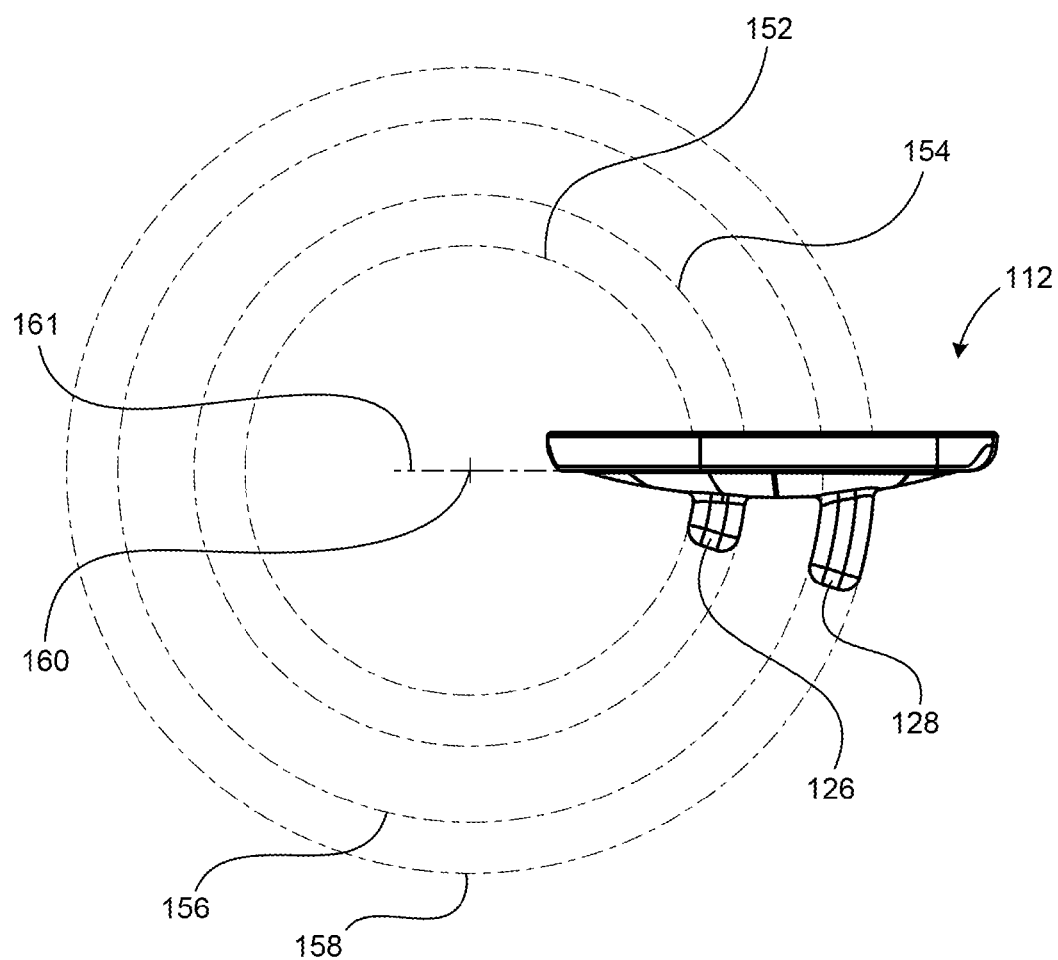
FIG. 28 is a side view of the lateral tibial implant shown in FIG. 21 depicting the relationship of certain of its components.
Figure 29:
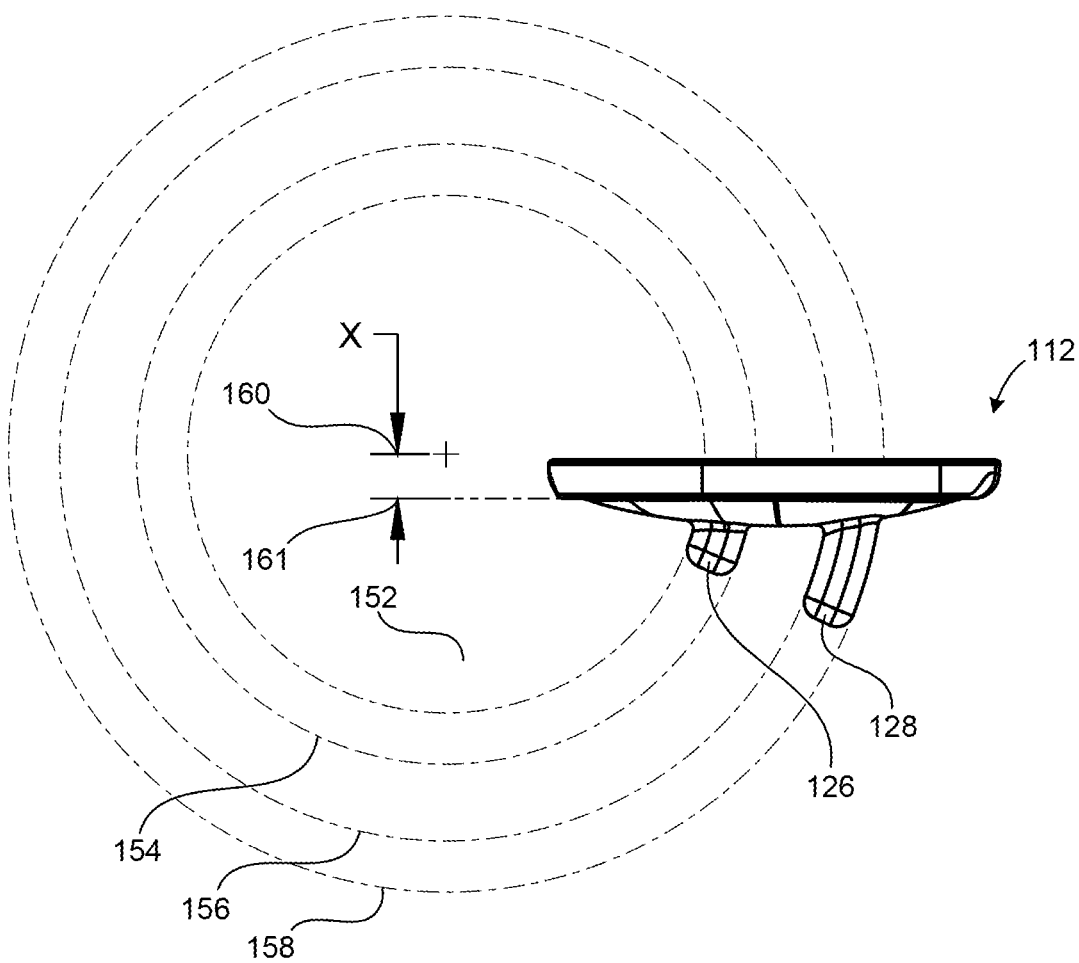
FIG. 29 is a side view of another embodiment lateral tibial implant similar to that shown in FIG. 21 depicting the relationship among certain of its components.
Figure 30:
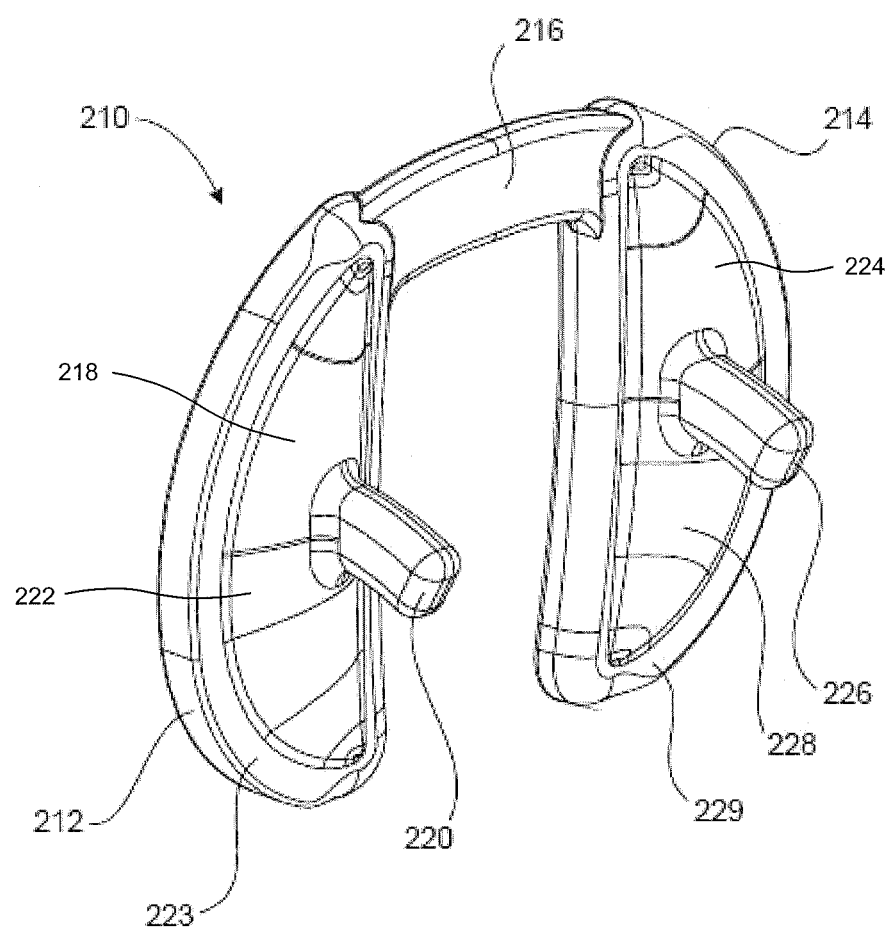
FIG. 30 is a perspective view of a bi-cruciate retaining ("BCR") tibial implant according to another embodiment of the present invention.
Figure 31:
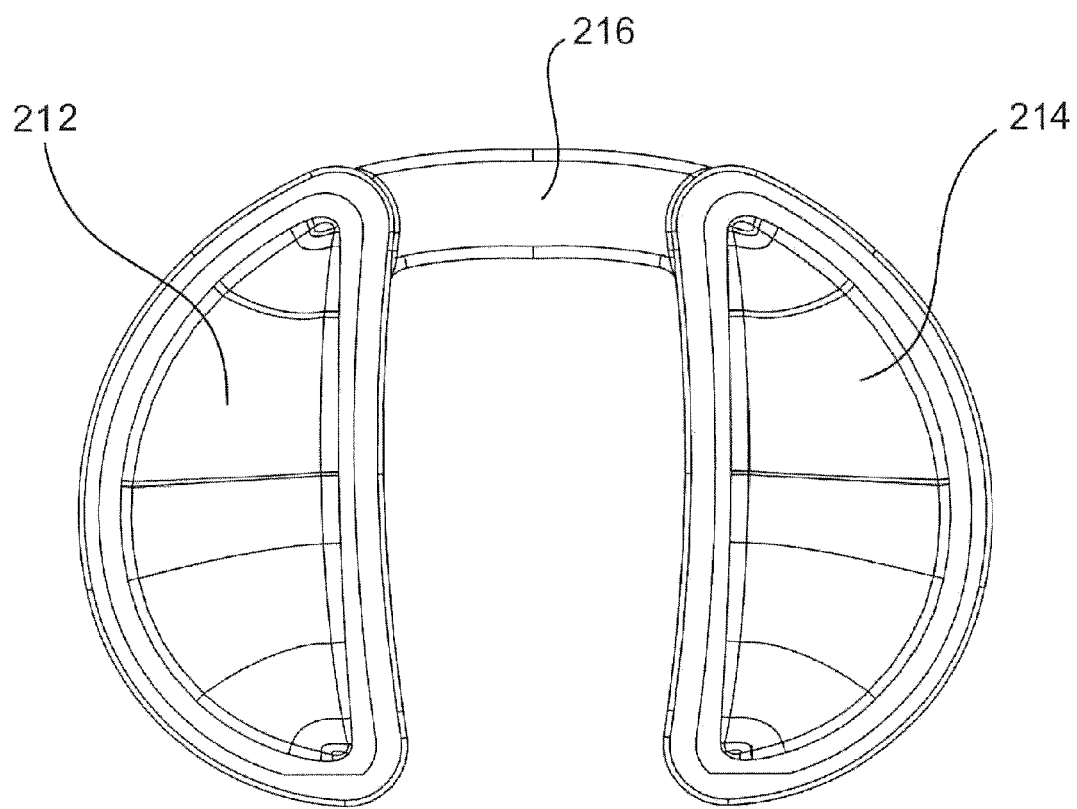
FIG. 31 is a top view of the BCR implant shown in FIG. 30.

It should be understood that both implants 112, 114 are designed for implantation on the proximal portion of the tibia in a similar fashion as are above-discussed femoral condyle implants 12, 14. With reference to FIG. 28, implant 112 is shown, with a posteriorly and anteriorly facing surfaces of peg 126 being curved along imaginary concentric circles 152 and 154, respectively, and posteriorly and anteriorly facing surfaces of peg 128 being curved along imaginary concentric circles 156 and 158, respectively. Those four circles are concentric about a center or pivot point 160 that is located posterior to implant 112. In addition, pivot point 160 is in line with a plane 161 extending along the flat surface of run out 131. This is contrary to the depiction of FIG. 29, where pivot point 160 is located posterior to implant 112, but offset from the plane 161 along run out 131. Although both embodiments offer an implantation procedure similar to the above-discussed femoral implants, it should be noted that the offset nature of the pivot point in FIG. 29 may allow for ease of insertion of a component in a small working volume. For instance, offsetting the pivot point may allow for easier insertion of the implant into small spaces, which is important in certain surgical techniques such as minimally invasive techniques. It should be understood that this concept may be employed in any of the implant designs discussed herein.

FIGS. 30-36 depict a bi-cruciate retaining ("BCR") tibial implant for use in surgeries where the anterior and posterior cruciate ligaments are spared, or a suitable synthetic ligament is employed. BCR implant 210 includes tibial components 212 and 214, which are attached via a bridging component 216. Both components 212 and 214 include a base plate portion (which are the portions connected together via bridging portion 216) and insert portions, in similar fashion as above-discussed tibial implants 112, 114. The base plate of component 212 includes a bone facing surface 218, which in turns includes a peg 220, a domed surface 222 and flat run out 223. Likewise, component 214 includes a bone facing surface 224 that in turns includes a peg 226, a domed surface 228 and a flat run out 229. As in the above-discussed tibial implants, flat run outs 223 and 229 surround domed surfaces 222 and 228, respectively.

Figure 32:
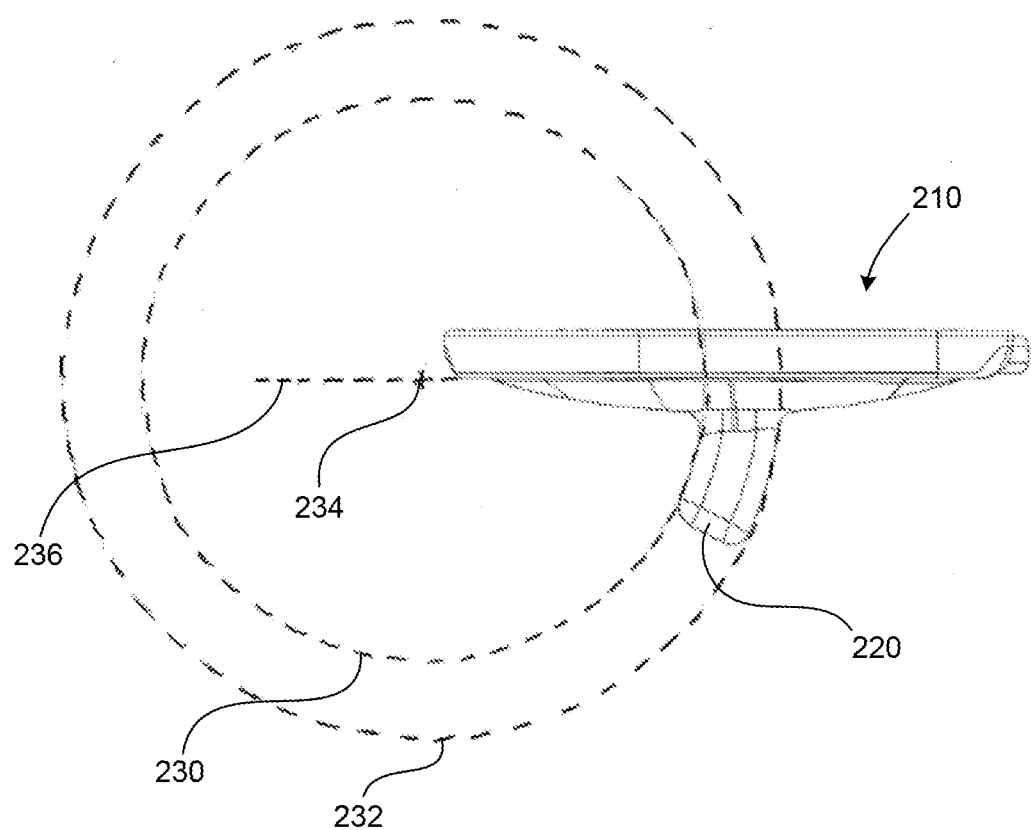
FIG. 32 is a side view of the BCR implant shown in FIG. 30 depicting the relationship among certain of its components.
Figure 33:
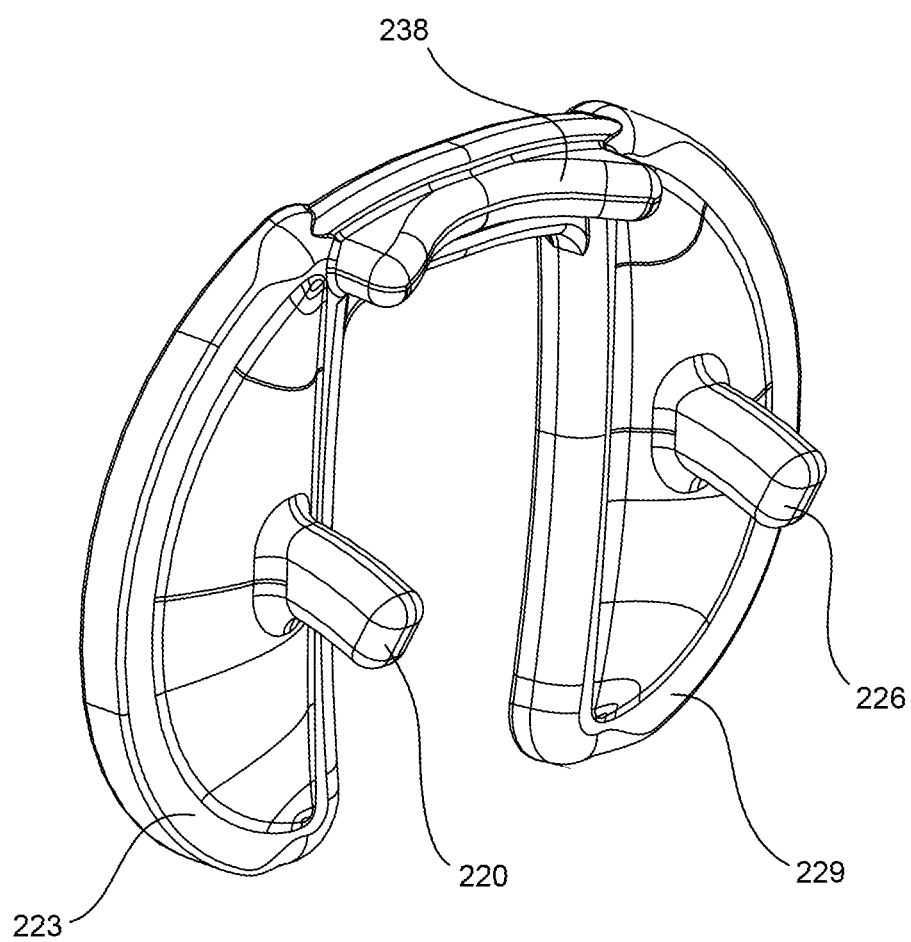
FIG. 33 is a perspective view of a BCR implant according to another embodiment of the present invention.
Figure 34:
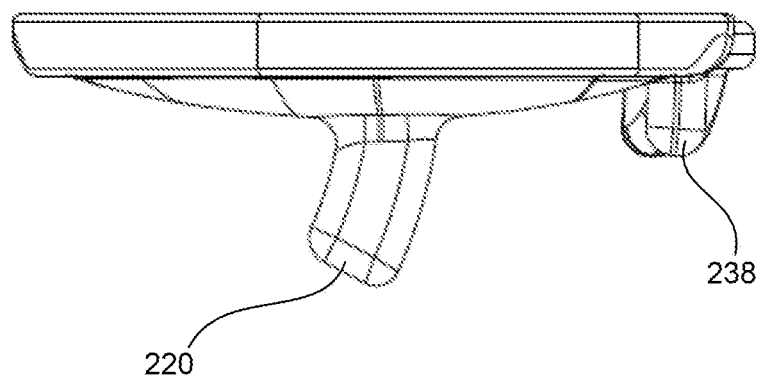
FIG. 34 is a side view of the BCR implant shown in FIG. 33.
Figure 35:
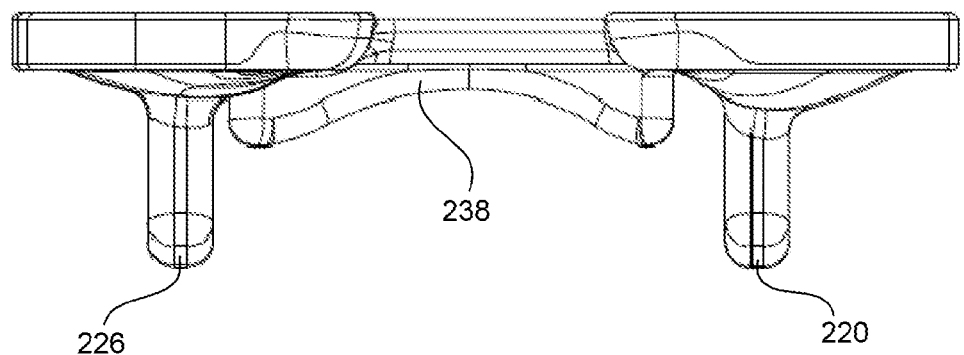
FIG. 35 is a front view of the BCR implant shown in FIG. 33.

Turning to FIG. 32, it is shown that implant 210 exhibits a similar construction to the above-discussed femoral and tibial implants in that pegs 220 and 226 (only component 212 is shown in the figure) includes a posterior facing surface curved along a circle 230 and an anterior facing surface curved along a circle 232. Those circles are concentric about a pivot point 234, which is situated posterior to the implant but along a plane 236 extending along run out 223. Thus, implant 210 may be implanted in a similar fashion as in the above-discussed implants. Likewise, implant 210 can exhibit any of the modifications discussed above in connection with the femoral and tibial implants. For instance, pivot point 234 could both be located posteriorly and offset from plane 236, as in the above-discussed tibia implant depicted in FIG. 29. Moreover, it should be understood that the tibia can be prepared to receive implant 210 in a similar fashion as it is in connection with the above-discussed tibia implants.

Figure 36:
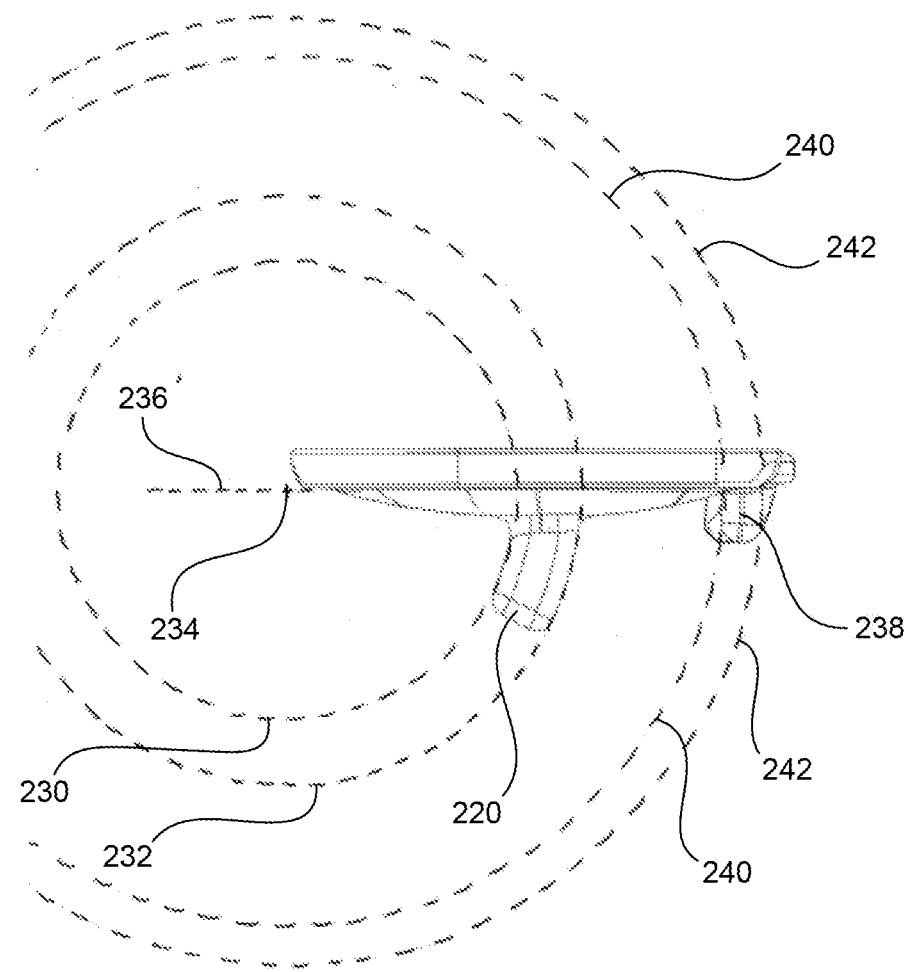
FIG. 36 is a side view of the BCR implant shown in FIG. 33 depicting the relationship among certain of its components.

FIGS. 33-36 depict a variation of implant 210 where an anterior keel 238 is provided on bridging component 216. As shown in FIG. 36, this component includes a posterior facing surface defined by a circle 240 and an anterior facing surface defined by an imaginary circle 242, those circles being concentric about pivot point 234 along with circles 230 and 232 defined by peg 220. Effectively, anterior keel 238 acts in a similar fashion as do the second pegs discussed above in connection with the femoral and tibial components. With specific reference to FIG. 35, it is shown that keel 238 is shallower toward its center to avoid disruption of an eminence of the proximal portion of the tibia. This construction requires less of the eminence to be resected to receive keel 238, which in turn, lessens the chance of the anterior cruciate ligament pulling away from the eminence or the eminence fracturing under the pressure created by the pulling force created by the anterior cruciate ligament.

Although certain embodiment BCR implants are shown and described herein, other BCR implant designs may be employed in accordance with the present invention. For instance, while maintaining the structures facilitating the implant-bone connection, BCR implants could retain other structures such as are taught in U.S. patent application Ser. No. 12/987,380, the disclosure of which is hereby incorporated by reference herein.

Figure 37:
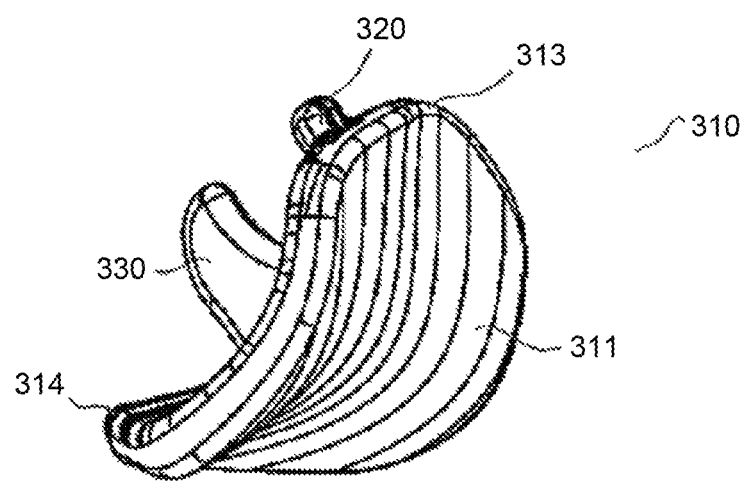
FIG. 37 is a perspective view of a patello-femoral implant according to another embodiment of the present invention.
Figure 38:
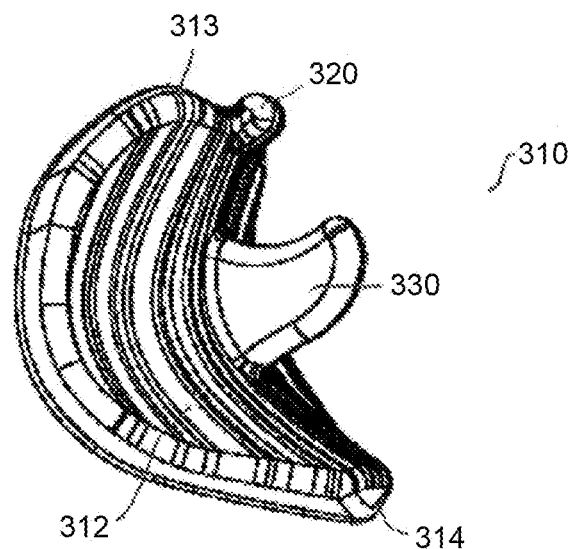
FIG. 38 is an alternate perspective view of the implant shown in FIG. 37.
Figure 39:
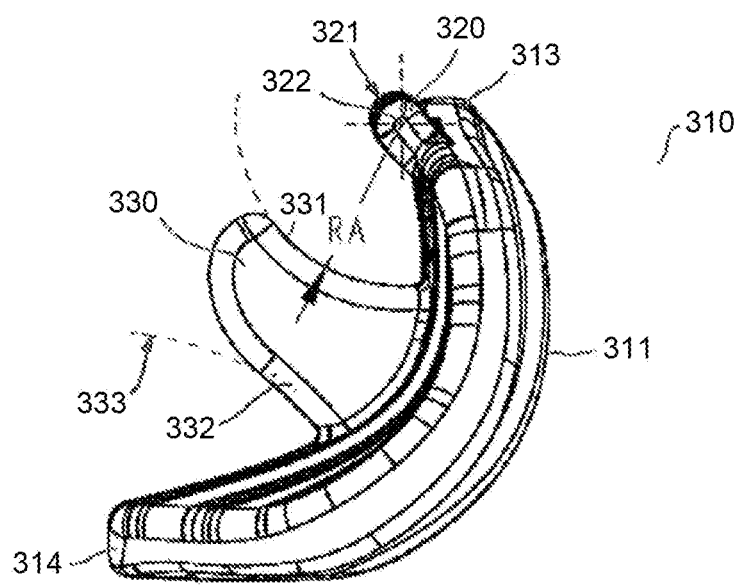
FIG. 39 is a side view of the implant shown in FIG. 37.

FIG. 37 depicts a patello-femoral implant 310. FIGS. 37-39 illustrate different perspective views of one embodiment of a patello-femoral prosthetic implant 310. Like the above-discussed implants, implant 310 may be manufactured from cobalt chrome, titanium, polyethylene, PEEK or other known implantable materials. Implant 310 includes an articular surface 311, a bone contacting surface 312, an anterior end 313 and a posterior end 314. The articular surface may be equivalent to that described in U.S. Patent Application 2010/0222781, the disclosure of which is hereby incorporated by reference in its entirety. Implant 310 further includes a primary peg 320 and a fixation feature 330. Once implanted, articular surface 311 of implant 310 is designed to replace the diseased articular cartilage of the trochlear groove of the patella-femoral joint, and will function by articulating with either a native or prosthetic patella implant.

Bone contacting surface 312 is designed to interface with the resected region of the trochlear groove. As with the above-discussed implants, the resected region of the cartilage and bone may be of planar or non-planar geometry.

Primary peg 320 is comprised of a primary peg radius 321 that has a primary peg center 322. The primary peg may have an elongate structure which extends from the bone contacting surface, as shown in the current embodiment. Further, the elongate structure may be straight, angled or curved with respect to the anterior end of the implant. In an alternate embodiment, primary peg 320 and the associated radius 321 and center 322 geometries may be built into the peripheral rim of the implant. In still further embodiments, there may not be a physical primary peg structure, but rather a theoretical primary peg center 322 which will serve as a geometric reference for various implant fixation features which are described herein. A physical or theoretical primary peg center may be located on any region of the implant including, but not limited to the anterior end, posterior end, medial end, and lateral end.

Fixation feature 330 is an elongate member extending from the bone contacting surface 312. In the embodiment shown, feature 330 is a bone peg including an anterior surface 331 and a posterior surface 332, both extending from bone contacting surface 312. Anterior surface 331 has an anterior surface radius RA, forming a concentric geometry about the primary peg center 322. In the embodiment shown, posterior surface 332 has a posterior surface radius 333 which is not concentric about primary peg center 322. In alternate embodiments, posterior surface 332 may be concentric about primary peg center 322.

It should be noted that any concentric geometric regions of either anterior surface 331 or posterior surface 332 may occupy a portion of the respective surfaces. For example, in one embodiment the concentric geometry on anterior surface 331 may cover approximately 50 percent of anterior surface 331 as seen from a side view perspective. In an alternate embodiment, approximately 100 percent of anterior surface 331 may be covered by a concentric geometry as seen from a side view perspective. The coverage may range from 25 percent to 100 percent of coverage of any concentric or non-concentric geometries.

FIGS. 40a-40d are a series of cross-sectional views illustrating the method of implantation for patello-femoral implant 10. Step 1 (FIG. 40a) of this method involves preparation of the distal femur 1. In this embodiment, the prepared boned surface is a non-planar resected bone surface 340, a resected region for receiving the primary peg 341 and a resected region for receiving fixation feature 342. In step 2 (FIG. 40b), primary peg radius 321 contacts the posterior aspect of the resected bone for receiving the primary peg 320. In step 3 (FIG. 40c), the implant is rotated about the primary peg radius 321 until fixation feature 330 enters the resected region for receiving fixation feature 342. Step 4 (FIG. 40d) illustrates a view of the implant 10 fully implanted.

During this method of implantation, an implantation path 350 is formed by following the primary peg center 322. Path 350 is a primary approach path until final seating which occurs when path 350 is substantially a curved path. The approach path may follow various paths, an example of which is a linear path. When an implantation path 350 is predetermined, the primary peg center 322 remains coincident with the implantation path. While peg center 322 progresses about the implantation path, the implant may rotate, thus the fixation feature 330, with concentric geometries by rotating about a path concentric to peg center 322. When in the final position, there is an over resected bone region 343 at the posterior aspect of primary peg 320. Further, the design of the anterior surface radius RA and posterior surface radius 333 allows for implantation of fixation feature 330 without the need for bone over-resection in this region. This is noted because when the knee moves through a range of motion the patella (either native or prosthetic) will transfer the variable and increasing loads through the implant 10. Given that the over resected bone region 343 is located on the posterior aspect of the primary peg 320, load will be transferred directly to the bone. Thus, this implant design will remain locked in place and minimize the risk of implant loosening.

Further regarding the implantation path 350, this unique path 350 geometry allows for positive seating of the implant into its proper position and results in an optimized final position of peg 320 and fixation feature 330. Implantation path 350 is substantially linear as the implant approaches the prepared bone. Path 350 then becomes substantially curved as the implant is finally seated and therefore locked into position. Alternately stated, the implant travels along a path 350 where the primary peg center 322, physical or theoretical, is preferably coincident with the implantation path. The orientation of the implant to the path is maintained throughout, such that the implant may rotate about the peg center 322 when traveling about a substantially curved, or linear, section of the implantation path. This rotation forms a concentric arcuate pathway of implantation.

Figure 41:
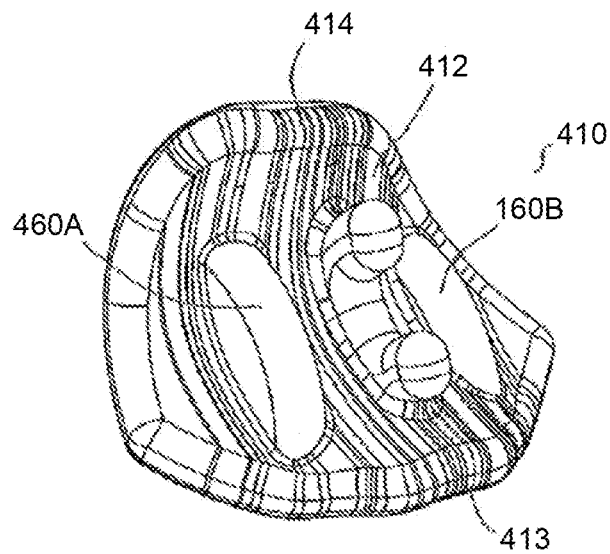
FIG. 41 is a perspective view of another embodiment a patello-femoral implant of the present invention.
Figure 42:
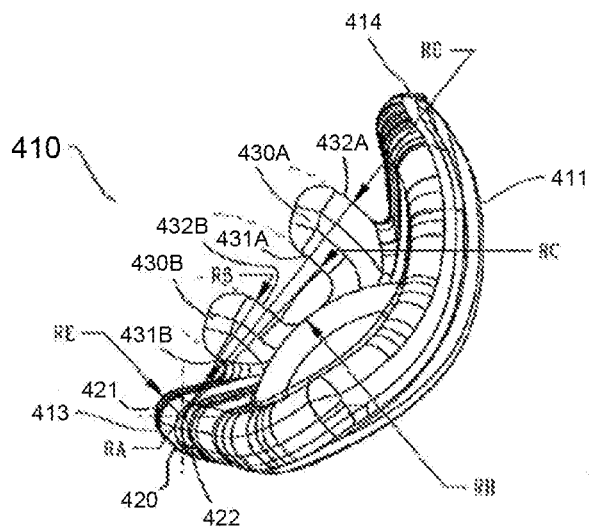
FIG. 42 is a side view of the implant shown in FIG. 41.

FIGS. 41 and 42 illustrate another embodiment of a patello-femoral prosthetic implant 410. Implant 410 includes an articular surface 411, a bone contacting surface 412, an anterior end 413 and a posterior end 414. Implant 410 further includes a primary peg 420, fixation features 430a and 430b and elements 460a and 460b. Primary peg 420 has a primary peg radius 421 and center 422. In this embodiment, the peg 420 is built into the periphery of the anterior end 413 of the implant 410. Fixation features 430a and 430b have respective anterior surfaces, 431a and 431b, and posterior surfaces, 432a and 432b. Surfaces 431a, 431b, 432a and 432b are designed with concentric radii (RA, RB, RC and RD) about the primary peg center 422.

Elements 460a and 460b are protrusions from bone contacting surface 412. The function of these elements is to provide additional fixation, strength and/or stability to implant 410. In this embodiment each element 460 has a radius of curvature, RH. RH may be different for each element, 460a and 460b. Further, RH has no relation to concentric radii: RA, RB, RC and RD.

The method of implantation of implant 410 is consistent with that previously described for implant 10. The primary peg center 422 remains coincident about an implantation path and implant 410 may rotate about primary peg center 422. An aspect of differentiation is that bone may need to be over resected along the posterior aspect of each fixation feature, 430a and 430b, because of the concentration radii relation to the peg center 422 on their respective posterior surfaces, 432a and 432b.

Other embodiment patello-femoral implants are envisioned, in which there will be at least one fixation feature, but there also may be a plurality of fixation features. These features will each have an anterior surface and a posterior surface with a relation to a primary peg center. Similarly, there may be none, one or a plurality of elements to provide additional stability. Still further, the peg geometries may include those as described in U.S. Pat. No. 7,294,149, the disclosure of which is hereby incorporated by reference in its entirety. Further, peg shapes may be cylindrical, hexagonal, cruciform, square, or other such geometries. The method of implantation will be consistent with the methods previously described where the primary peg center follows and remains coincident along an implantation path and the implant may rotate about the primary peg center, then locking into its final position.

Figure 43:
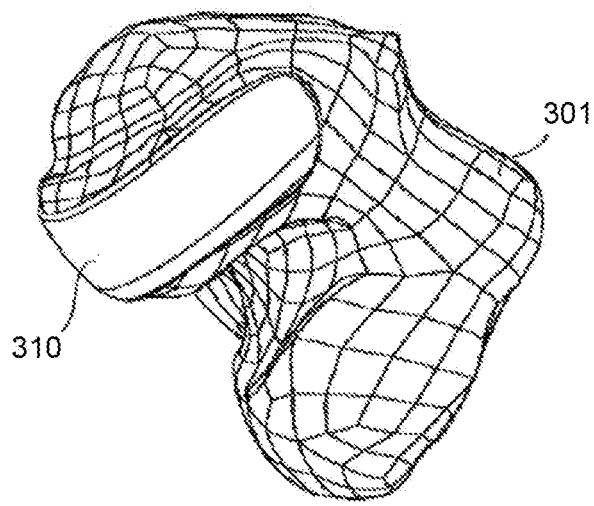
FIG. 43 is a perspective view of one embodiment of a distal femoral bone with a unicondylar implant of the present invention.
Figure 44:
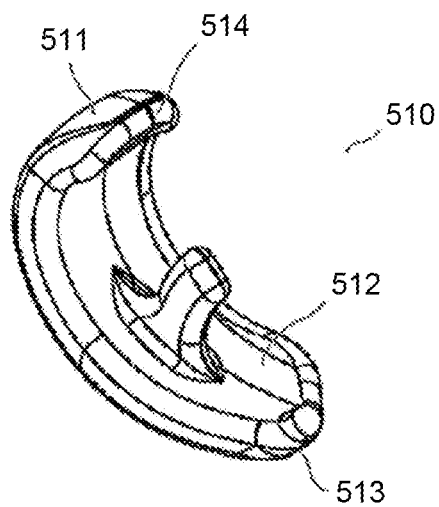
FIG. 44 is a perspective view of the unicondylar implant shown in FIG. 43.
Figure 45:
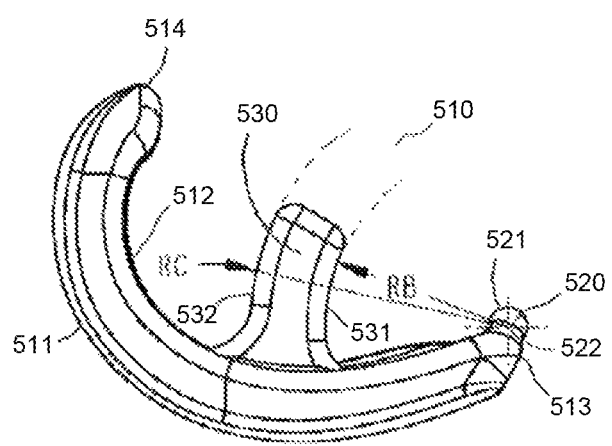
FIG. 45 is a side view of the implant shown in FIG. 43.

Another embodiment femoral implant 510 similar to above-discussed implants 12 and 14 is depicted in FIGS. 43-45. The particular implant shown in those figures is designed as a unicondylar knee replacement ("UKR") for a unicondylar knee arthroplasty procedure. However, like implants 12 and 14, implant 510 may be utilized in a system such as is shown in FIG. 1. In the embodiment shown, the articular surface of implant 510 may have a sagittal geometry similar to that described in U.S. Pat. No. 5,824,100, the disclosure of which is hereby incorporated by reference in its entirety. Once implanted, unicondylar implant 510 will articulate with a prosthetic tibial implant.

FIG. 44 depicts unicondylar implant 510, which includes an articular surface 511, a bone contacting surface 512, an anterior end 513 and a posterior end 514. FIG. 45 is a side view of implant 510, where primary peg 520 and a fixation feature 530 can be seen. Peg 520 has a primary peg radius 521 and a primary peg center 522. Fixation feature 530 includes an anterior surface 531 and posterior surface 532 extending from the bone contacting surface 512. Further, anterior surface 531 has a radius RB and posterior surface 532 has a radius RC. Radii RB and RC are concentric about primary peg center 522. As previously described, concentric Radii RB and RC on respective surfaces 531 and 532, may cover between the range of 25 to 100 percent of the surface as seen from a side view perspective. Of course, it is contemplated that Radii RB and RC may cover less than 25 percent of the surface. Further, the concentric coverage on anterior surface 531 may be the same as, or different than, the concentric coverage on posterior surface 532.

Figure 46A:
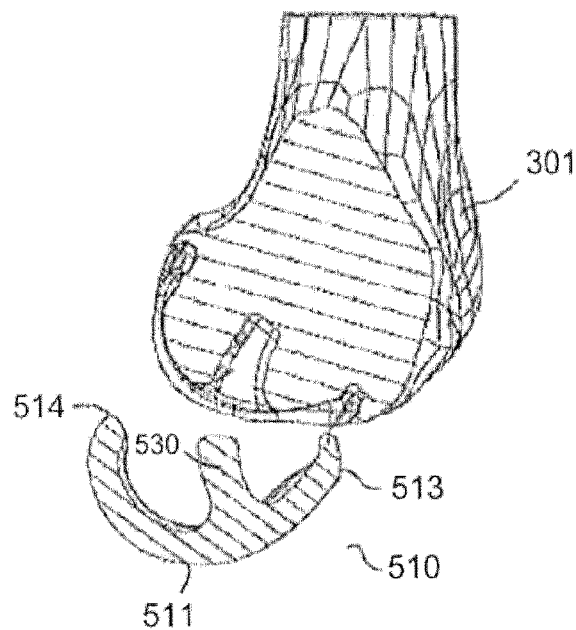
FIGS. 46a-46c are a series of cross-sectional views illustrating a method of implantation for the implant shown in FIG. 43.
Figure 46B:
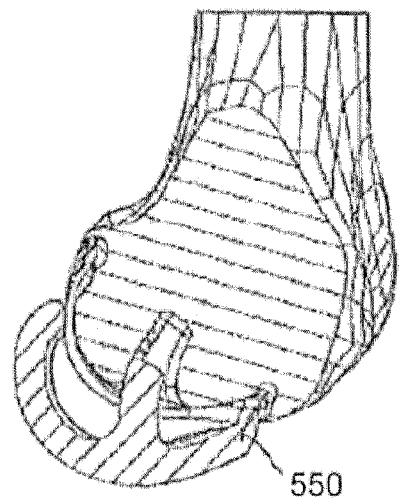
Figure 46C:
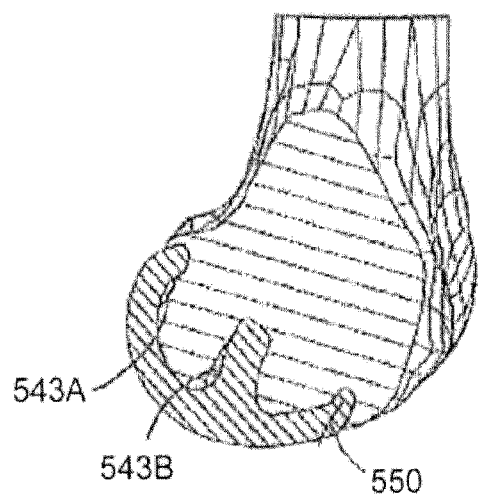

FIGS. 46a-46c illustrate a method of implantation for implant 510. Similar to the methods described above, primary peg center 522 is coincident along an implantation path 550. Implant 510 is rotated about center 522, while moving about implantation path 550 and into a final locked position. In this embodiment, the path may be substantially curved, and may or may not have a linear aspect. What is differentiated about this specific method is the specific location of the over resected bone regions, 543a and 543b. Region 543a is located on the anterior aspect of the bone contacting surface 512 of the poster condyle. Region 543b is located on the posterior aspect of the posterior surface 532 of the fixation feature 530.

Figure 47:
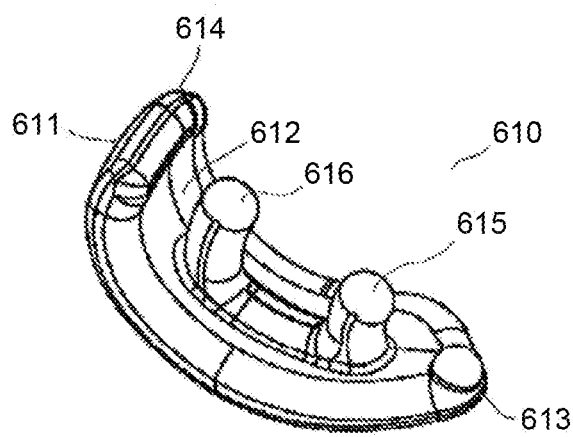
FIG. 47 is a perspective view of another embodiment of a unicondylar implant of the present invention.
Figure 48:
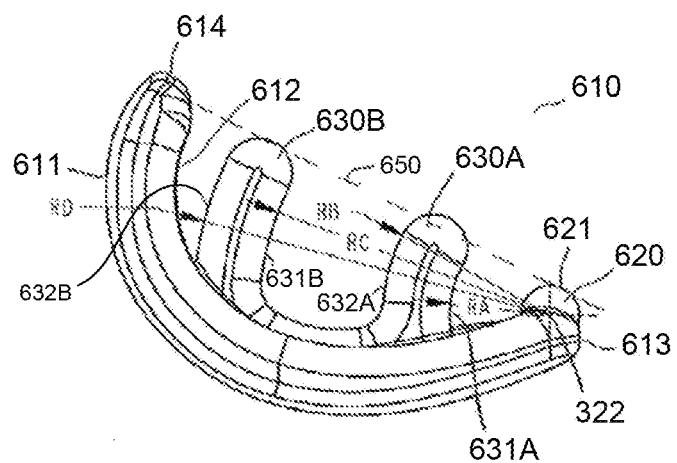
FIG. 48 is a side view of the implant shown in FIG. 47.
Figure 49:
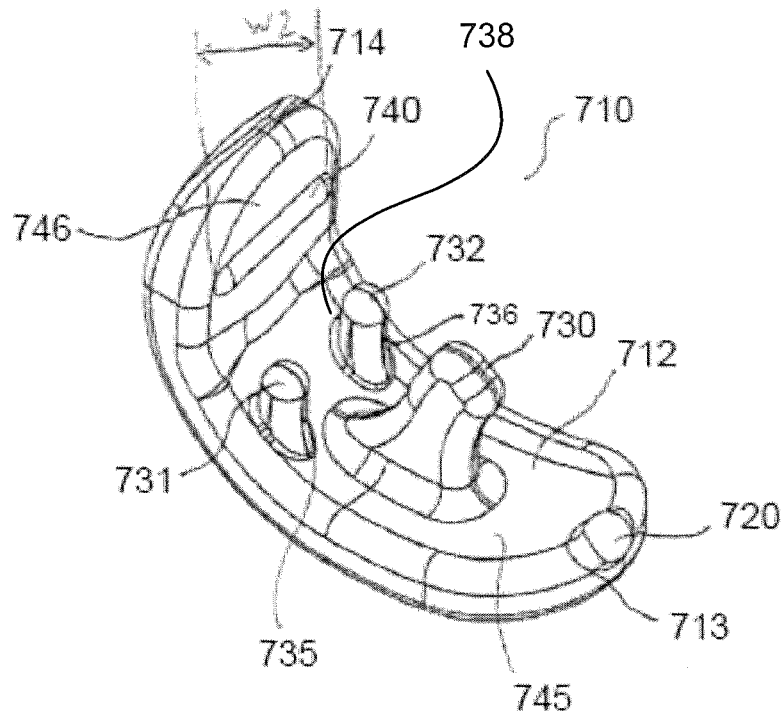
FIG. 49 is a perspective view of another embodiment of a unicondylar implant according to the present invention.
Figure 50:
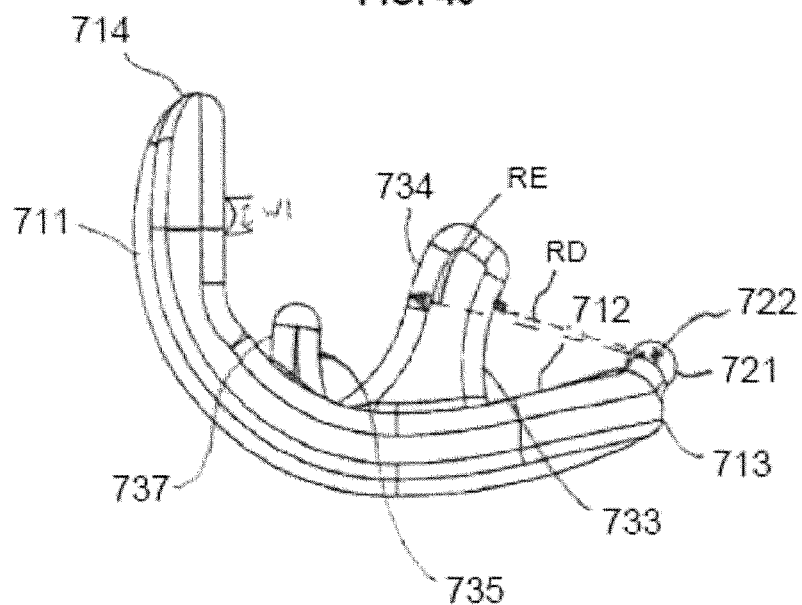
FIG. 50 is a side view of the implant shown in FIG. 49.
Figure 53:
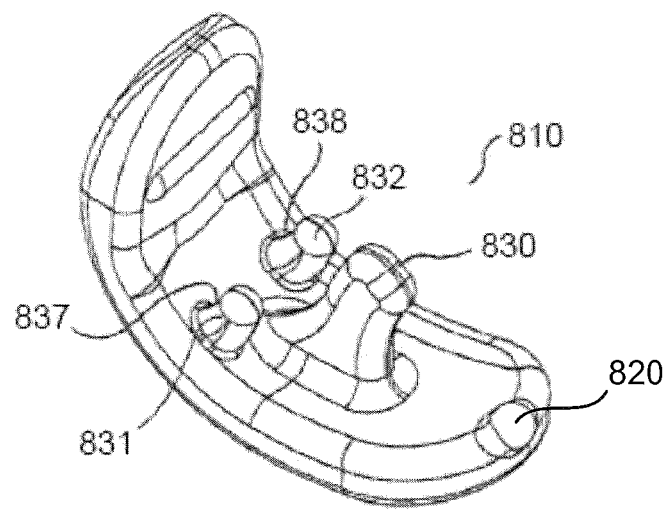
FIG. 53 a perspective view of another embodiment of a unicondylar implant according to the present invention.
Figure 54:
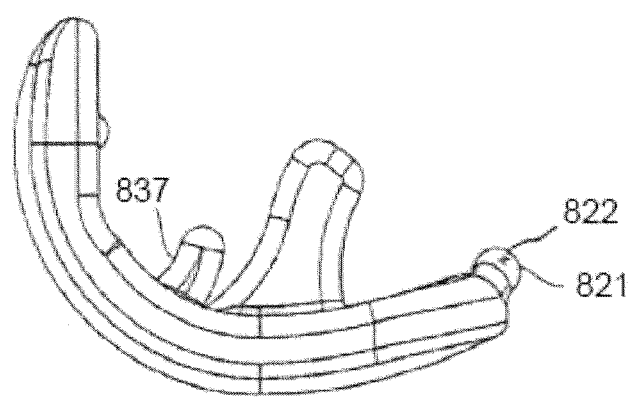
FIG. 54 is a side view of the implant shown in FIG. 53.

FIGS. 47 and 48 are perspective views of another embodiment of a unicondylar implant 610, which includes an articular surface 611, a bone contacting surface 612, an anterior end 613 and a posterior end 614. Here, two peg features 615 and 616 may each have a similar configuration and size diameter for the length of the peg. In particular, peg features 615 and 616 exhibit a rounded rectangular shape. Alternately, the configuration of peg features 615 and 616 may be different, constant, tapered, or any combination thereof. For instance, in other embodiments, the peg features may be cylindrical with constant or non-constant diameters.

As best shown in FIG. 48 implant 610 further includes a primary peg 620 and fixation features, 630a and 630b. Primary peg 620 includes a primary peg radius 621 and a primary peg center 622. Fixation features, 630a and 630b, each comprise respective anterior surfaces, 631a and 631b, and posterior surfaces, 632a and 632b, which extend from the bone contacting surface 612. Surfaces 631a, 632a, 631b and 632b have radii RA, RB, RC and RD which are concentric about peg center 622. As previously mentioned, the percent surface area concentric geometry coverage may range from 25 to 100 percent of the respective anterior and posterior surfaces as seen from the side view. In one embodiment, the percentage of concentric geometry coverage may be the same for all surfaces of all pegs. In an alternate embodiment, the percentage of concentric geometry coverage may be different for all surfaces of all pegs. It is understood that there can be any combination of percentage of concentric geometry coverage on any respective surface and for on any respective peg feature.

Angled line 650 shows the relationship between primary peg 620 and fixation features 630a and 630b. Line 650, as illustrated, is a straight line between a tangent point of primary peg radius 621 and a tangent point on the distal most tip of feature 630b. In the embodiment shown, the length of 630a extends beyond line 650. In other embodiments, a primary peg 620 and all fixation features, 630a and 630b, would extend to a length ending on angled line 650. Further, as moving away from a physical or theoretical center point, one, two or more fixation features may increase in size. In yet other embodiments, fixation feature 630a may not extend to angled line 650. This relationship of fixation features may further include posterior end 614, where end 614 may extend beyond, to or below line 650. In yet other embodiments of angled line 650, the origin of the feature may be referenced from center 622 instead of a tangent point.

In another embodiment of line 650, it may be formed by connection to either a center point (not show) of a distal radius of a fixation feature or a tangent point of a fixation feature. This angled line relationship may be included in all embodiments of the contemplated inventions and is important to the function of the implant because this relationship of peg and feature length will dictate when the prepared bone is contacted by the implant during implantation. Methods of implantation for implant 610 are consistent with those previously described.

FIGS. 49-52 depict another embodiment unicondylar implant 710 and an associated interface within a distal femoral bone 701. Implant 710 includes an articular surface 711, a bone contacting surface 712, an anterior end 713 and a posterior end 714. Implant 710 preferably has a primary peg 720 having a primary peg radius 721 and a primary peg center 722. Implant 710 preferably further includes a first fixation feature 730, a second fixation feature 731 and a third fixation feature 732, each extending from bone contacting surface 712. First fixation feature 730 has an anterior surface 733 and a posterior surface 734, wherein anterior surface 733 follows a radius RD and posterior surface 734 follows a radius RE. Radii RD and RE are concentric about peg center 721.

Second fixation feature 731 and third fixation feature 732 are both offset posteriorly with respect to first fixation feature 730. Further, fixation features 731 and 732 are offset in respective medial and lateral regions of the implant with respect to first fixation feature 731. In the embodiment shown, fixation features 731 and 732 are spaced equally in the respective medial and lateral directions. In alternate embodiments, the offset spacing may be different with respect to any of, or any combination of the posterior, medial and lateral directions.

Second fixation feature 731 and third fixation feature 732 further include respective anterior surfaces 735 and 736, and respective posterior surfaces 737 and 738. Posterior surface 738 of third fixation feature 732 is not shown. In the embodiment shown, anterior surfaces 735 and 736, and posterior surfaces 737 and 738 include a geometry that is concentric about the primary peg center 721. However, in alternate embodiments, any one of, or combination of surfaces 735, 736, 737 or 738 may include geometry concentric about primary peg 721. Yet other alternate embodiments of fixation features 730, 731 or 732 may include any of the geometric relationships previously described.

Further, implant 710 includes a posterior locking feature 740. Posterior locking feature 740 extends from bone contacting surface 712 and has a first width W1 and a second width W2. In the embodiment of feature 710 shown, the profile is a substantially curved extrusion with second width W2 being greater than first width W1. In alternated embodiments, width W2 may be substantially equal to width W1. In yet other embodiments, there may be multiple posterior locking features spaced located on the posterior aspect of the implant.

In the embodiment shown, bone contacting surface 712 includes a curved region 745 and a flat region 746. Curved region 712 extends from the anterior end 713 and includes fixation features 730, 731 and 732. Flat region 746 extends from posterior end 714 and includes posterior locking feature 740. Further, curved region 745 comprises a significant portion of bone contacting surface 712 compared to flat region 746. Specifically regarding this embodiment, bone contacting surface 712 is comprised of approximately 75 percent curved region 745 and 25 percent flat region 746. In alternate embodiments, the area of surface 712 may be comprised of different percentage ratios of curved region 745 to flat region 746. For example, in an alternate embodiment, the area coverage of surface 712 may be comprised of approximately 50 percent curved region 745, compared to 50 percent flat region 746. In other embodiments, posterior locking feature 740 may extend from a curved region 745 of bone contacting surface 712.

Multiple cross-sections are shown to illustrate the final position of implant 710 onto bone 701. Referring to FIG. 51, a cross-sectional view through the first fixation feature 730 is shown. In the "Detail A" view, an interference region 750, clearance region 751 and contact region 752 are shown. Here, clearance region 751 is centrally located on the posterior surface 734 as shown in this side view. Further, the clearance region 751 comprises approximately 50 percent of posterior surface 734. In alternate embodiments, the clearance region may comprise between a range from 25 to 75 percent of the posterior surface. In all cases, clearance region 751 is preferably surrounded by contact regions as shown in the sagittal view. Interference region 750 is substantially centrally located on anterior surface 733 and is surrounded by contact regions as shown in FIG. 51. A resultant force L1 creates a biased press-fit at the implant-bone interface.

Referring to FIG. 51, a cross-sectional view through the first fixation feature 731 is shown. In the "Detail B" view, an interference region 755, clearance region 754 and contact region 756 are shown. Interference region 755 is shown in a approximately centrally located position on posterior surface 737 of fixation feature 731 and has an associated resultant force of L2 which creates a biased press-fit at the implant-bone interface. Here, interference region 755 approximately covers 50 percent of posterior surface 737, but may cover between 25 to 75 percent of posterior surface 737 in alternate embodiments. Interference region 755 is adjacent to clearance region 754 in one direction and is adjacent to contact region 756 in an opposite direction. As shown, contact region 756 continues about the anterior surface 735. In alternate embodiments, interference region 755 may be surrounded by contact regions. Although not shown, the cross-sectional view through fixation feature 732 is similar to that just described and has a resultant force of L3 (not shown) at an interference region.

With respect to the cumulative effect of the resultant forces L1, L2 and L3, force L1 acts on anterior surface 733 while forces L2 and L3 act on the respective posterior surfaces 737 and 738. Alternately stated, force L1 acts in an equal and opposite direction to the combination of resulting forces L2 and L3. The result of this biased press-fit loading pattern is a benefit in the initial fixation at the implant-bone interface. Here, the unique implant geometries and bone preparation enable the implant to essentially be held or gripped in place under the press-fit loading created by the sum of the resulting forces.

While the implantation of implant 710 onto prepared bone 701 is not shown, it would follow the implantation path philosophy previously described. Here, the physical peg center 722 is coincident along an implantation path. The implantation path may have linear and arcuate shapes. During implantation, peg center 722 remains coincident along the path while the implant rotates, thus rotating fixation features 730, 731 and 732 along the concentric arcs which are concentric about peg center 722. As the implant nears the end of the implantation path and the final seating is about to occur, peg center 722 translates, thus incorporating a cam like locking/interference of the first fixation feature 730 with bone 701. The fixation of feature 730 with bone 701 essentially creates a primary locking resultant force as represented by L1. As features 731 and 32 are seated into final position, a set of secondary locking resultant forces are established which are represented by L2 and L3. Force L1 may act in opposition to forces L2 and L3 to lock the implant to the bone and provide and enhanced initial fixation.

It should be noted that the resultant forces generated by an interference between the implant and bone may be achieved in various ways. The forces may be the result fully of the implant preparation, fully within the implant design, or a combination of the implant preparation and implant design. In any scenario, the a physical or theoretical center point would be coincident with an implantation path, the implant may simultaneously rotate about the center point and the final seating of the implant would have a plurality of resultant forces designed to enhance the initial fixation of the implant by locking it onto the bone.

FIGS. 53-56 depict yet another embodiment unicondylar implant 810 and associated interface within a distal femoral bone 801. Implant 810 has a primary peg 820 having a primary peg radius 821 and primary peg center 822. Implant 810 has three fixation features 830, 831 and 832. Features 831 and 832 have respective posterior surfaces 837 and 838 as shown. A key difference between implant 810 and those previously described, for instance, implant 710 (shown in FIGS. 49-52), is that posterior surface 737 is concentric about peg center 722, whereas posterior surface 837 is not concentric about peg center 822.

In FIG. 55, both illustrations marked "Detail C" are similar to those illustrations marked with "Detail A" previously described in FIG. 51. However, there are differences between illustrations marked "Detail D" in FIG. 56 and illustrations marked "Detail B" in FIG. 52. Regarding "Detail D," there is an interference region 855, which is surrounded by contact regions 856. Interference region 855 approximately covers 75 percent of posterior surface 837. Therefore, the geometry of the posterior surface 837 enables unique bone preparation and implant-bone interface contact. In contrast, "Detail B" in FIG. 52 includes interference region 755 surrounded by both a clearance region 754 and contact region 756. Further, region 755 covers approximately 50 percent of posterior surface 737.

Figure 59:
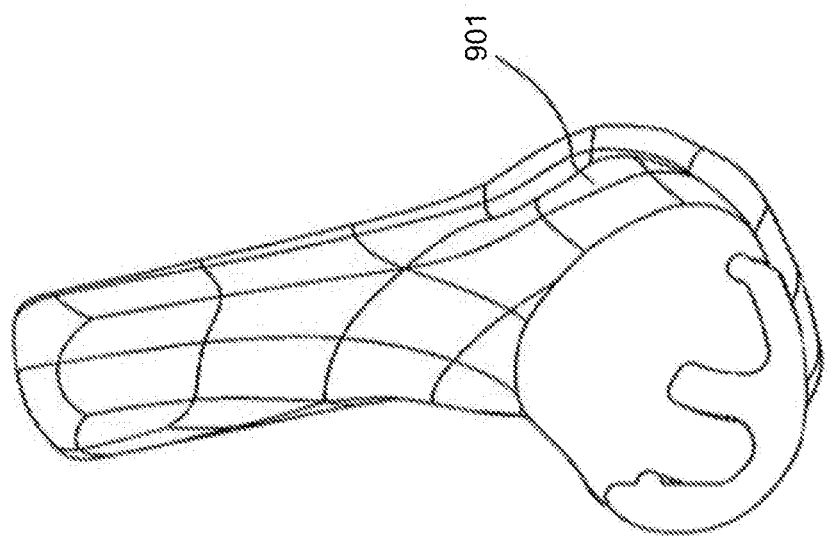
FIG. 59 is a partial cross sectional view of the implant of FIG. 57 implanted on a femur.
Figure 57:
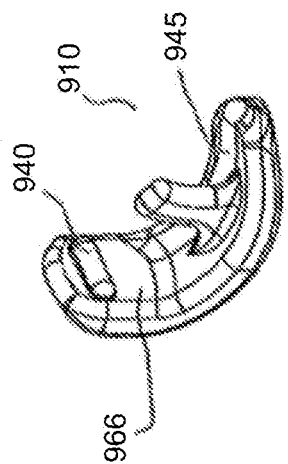
FIG. 57 is a perspective view of another embodiment unicondylar implant according to the present invention.
Figure 58:
FIG. 58 is a side view of the unicondylar implant shown in FIG. 57.

FIGS. 57-59 depict another unicondylar implant 910 and associated interface with a distal femoral bone 901. Implant 910 is similar to, and includes all features previously described with respect to implant 510. In contrast to implant 510, implant 910 contains both a flat bone contacting region 966 and a curved bone contacting region 945. Flat region 966 may enable easier preparation of the posterior distal femoral bone. Implant 910 also includes a posterior locking feature 940 located within flat region 966 and having a curved profile 941. Feature 940 is a locking feature that engages the bone late during implantation and provides additional stability. Profile 941 is designed with a geometry equivalent to that of a rotational preparation tool such as a burr. Feature 940 may have all of the features described with respect to posterior locking feature 740.

FIGS. 60-63 depict a tibial implant 1010 and associated interface within a proximal tibial bone 1001. Implant 1010 may be monolithic and made of polyethylene or other suitable material as shown, or it alternately may be a modular design including a polymeric insert component and a metal tray component. Implant 1010 preferably has a bearing surface 1011, a bone contacting surface 1012, an anterior end 1013, a posterior end 1014, an inner side 1015 and an outer side 1016. Bearing surface 1011 preferably has profile designed to articulate with an articular surface of a femoral prosthetic implant, such as a unicondylar implant as previously described. In the embodiment shown, implant 1010 contacts the bone on surface 1012, inner side 1015 and outer side 1016. Inner side 1015 may be substantially perpendicular to bone contacting surface 1012 as shown, or side 1015 may alternately have an angular relationship with surface 1012. Outer side 1016 contacts a small portion of proximal tibial bone 1002. In alternate embodiments, proximal tibial bone 1002 may be resected and therefore outer side 1016 would not be contacting bone.

Figure 63:
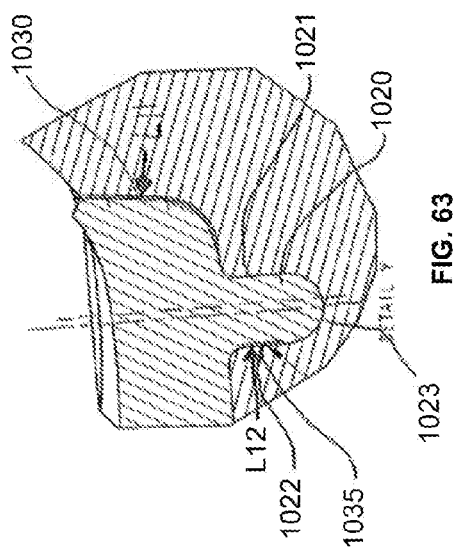
FIG. 63 is an enlarged cross sectional view of the implant and tibial bone of FIG. 60.
Figure 60:
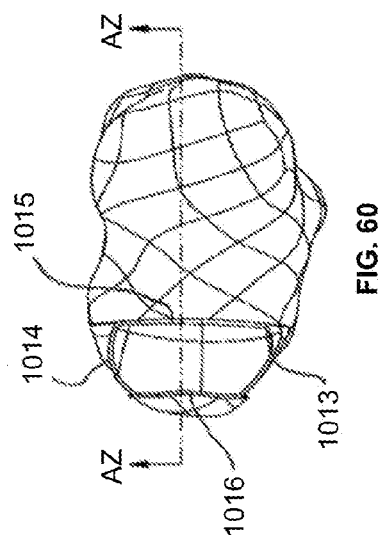
FIG. 60 is a top view of a tibial implant and associated interface within a proximal tibial bone according to another embodiment of the present invention.
Figure 62:
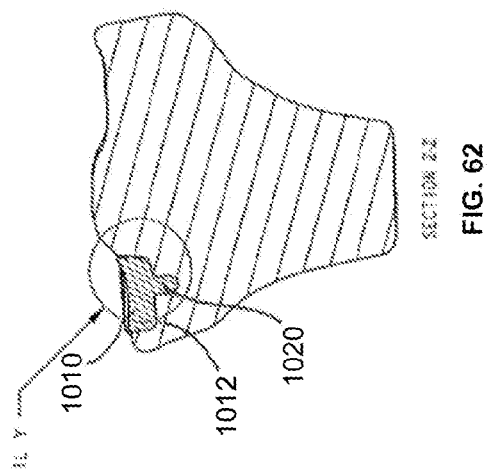
FIG. 62 is a cross sectional view of the implant and tibial bone of FIG. 60.
Figure 61:
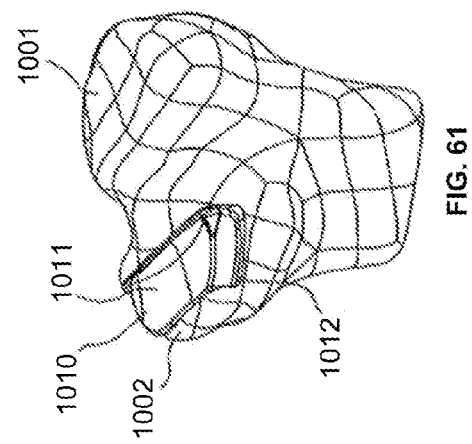
FIG. 61 is a perspective view of the implant and tibial bone of FIG. 60.

Referring specifically to FIG. 63, an elongate element 1020 preferably extends from bone contacting surface 1012 of implant 1010. As shown in this cross-sectional view, peg 1020 has a first side 1021, a second side 1022 and a distal end 1023. Element 1020 may have a generally cylindrical, hexagonal, or other geometric shape, including the peg geometries previously disclosed. Further, distal end 1023 may have many different geometries such as rounded (as shown), spiked, flared, tapered or other ending geometries. Further, a first interference region 1030 is shown and defined as the interface between inner side 1015 and an inner wall of bone 1001. First interference region 1030 has a resultant press-fit force of L11. A second interference region 1035 is shown and defined as the interface between second side 1022 and bone 1001. Second interference region 1035 has a resultant press-fit force of L12. During implantation of implant 1010 onto bone 1001, the second interference region 1030 drives the component toward the inner side thus creating the first interference region 1030. The resultant forces act to seat the implant in the appropriate medial/lateral location and further to provide improved initial fixation of the implant onto the bone. It should be noted that resultant forces L11 and L12 are offset from each other as shown.

Figure 64:
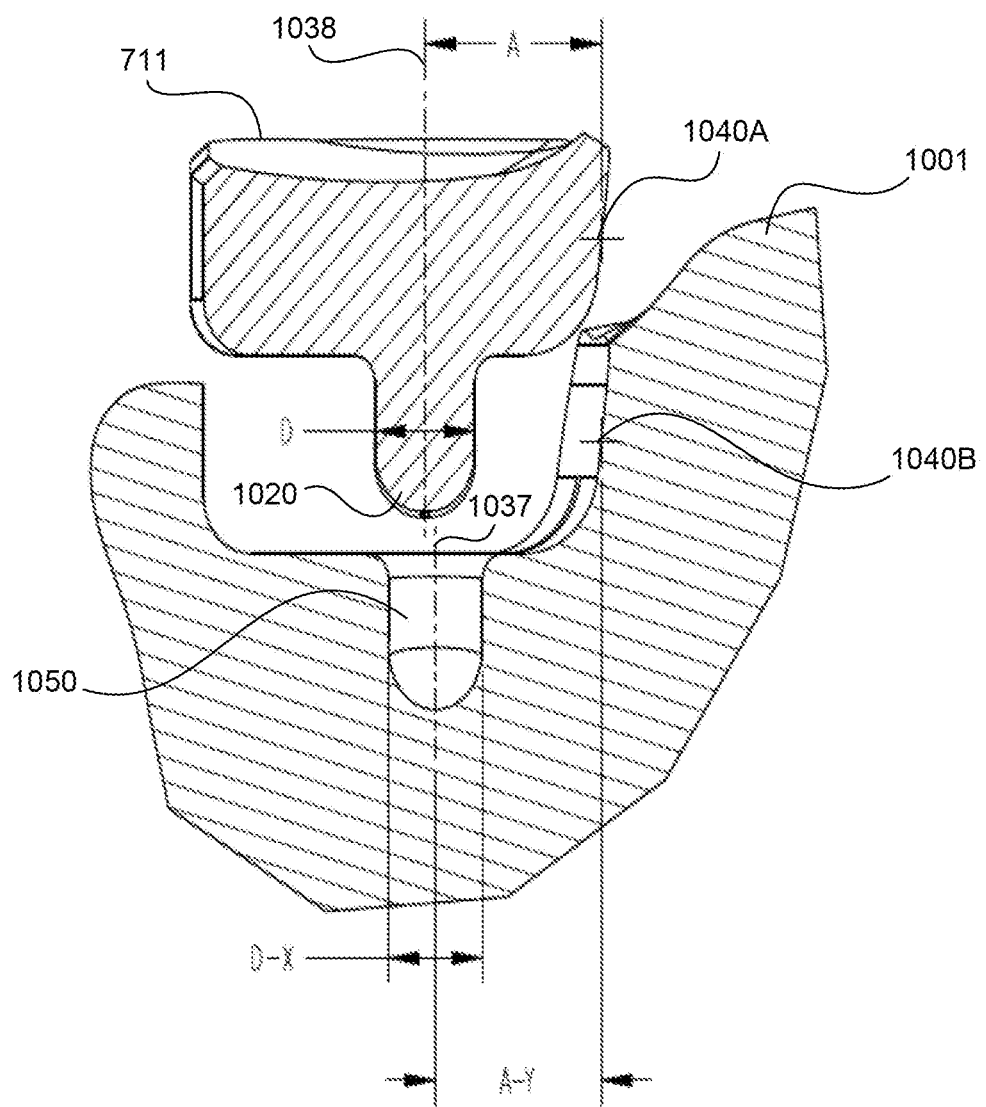
FIG. 64 is a cross-sectional view of the tibial implant shown in FIG. 60 further compromising geometric relationships between the implant and the bone.

FIG. 64 is a cross-sectional view of the tibial implant shown in FIGS. 60-63 further compromising geometric relationships between the implant and the bone. Element 1020 has an element central axis 1038 and a reference point 1040*a* on inner side 1015. Element 1020 has a width "d" and the distance from axis 1038 to reference point 1040*a* is "a". Prepared bone 1001 has cavity 1050 prepared for receiving peg 1020. Cavity 1050 has a cavity central axis 1037. Bone 1001 has a reference point 1040*b* which, when implant 1010 is fully seated will contact point 1040*a*. Cavity 1050 has a width of "d-x" and the distance from axis 1037 to point 1040*b* is "a-y". During implantation there is a press-fit of peg 1020 into cavity 1050. As point 1040*a* seats upon point 1040*b*, the difference between "a" and "a-y" and/or "d" and "d-x" results in an interference which biases the implant such that central axis 1038 is offset from axis 1037. This geometric relationship causes the respective interference loads and resultant forces previously described in FIG. 63.

Figure 65:
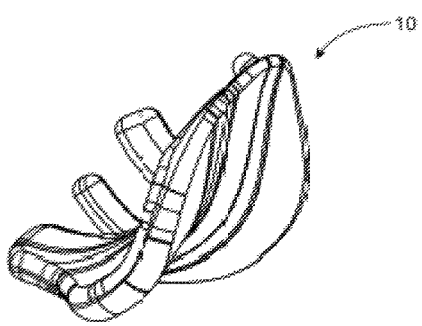
FIGS. 65-67 are different perspective views illustrating yet another patello-femoral implant according to another embodiment of the present invention.
Figure 67:
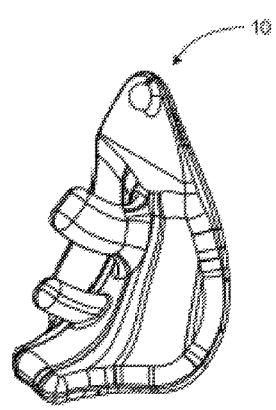
Figure 66:
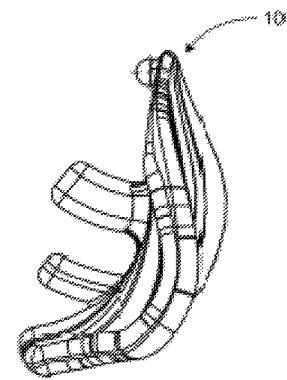

FIGS. 65-67 depict yet another embodiment patello-femoral prosthetic implant 10. FIG. 1 illustrates patello-femoral implant 10 in an implanted state, where it will articulate with either a native or prosthetic patella. Among the differences between implant 10 and, for instance, implant 310, is the inclusion of two pegs in place of fixation feature 330. However, implant 10 is largely implanted in the same fashion as the other patella-femoral prosethic implants discussed herein.

Although several of the embodiment implants discussed above are designed for engagement with prepared bone surfaces that do not exhibit planar surfaces, it should be understood that the implants could be modified to also engage with such planar surfaces. Moreover, although one method for preparing the bone surfaces to receive the implants of the present application could be the use of a milling instrument or the like (including a milling instrument coupled with a robot or the like), other methods may be utilized. For instance, reamers, saw blades, or other cutting instruments may be adapted to be utilized in the implantation procedures for the present implants.

Overall, the various invention embodiments described herein utilize a plurality of or at least one concentric shaped feature (fins, keels, pegs) having a specific relationship to a prepared bone. The relationships of the implant and bone contacting surface may be an interference fit, clearance or interference relationship. Further, this relationship serves to fixate, or lock, the implant to the prepared bone surfaces. Alternately stated, the locking resultant forces generated at the interference regions of the implant and bone, establish an enhanced initial fixation of the implant. The enhanced fixation is critical, especially in the zero to six month post-operative period when bone ongrowth and/or ingrowth occurs.

Moreover, as noted above, the various implants described above may be designed for a cemented application, and in such case, their respective bone facing surfaces may be finished with a treatment, such as grit blasting, which will optimize the mechanical attachment to bone cement or other known attachment materials such as bone adhesives. An example of a medical adhesive is described in U.S. Patent Application Nos. 2009/0318584, 2009/0280179, and 2010/0121459, the disclosure of which are all hereby incorporated by reference in their entirety. In cementless applications, the bone contacting surfaces of the various implants may be treated with bone growth agents such as peri-apetite or hydroxy-apetite. Further, the bone contacting surface may have an ingrowth structure such as beads or a porous metal structure. An example of a beaded ingrowth structure is described in U.S. Pat. No. 4,550,448, the disclosure of which is hereby incorporated by reference in its entirety. The porous metal structure may be manufactured from the technology described in U.S. Pat. Nos. 7,537,664, 7,674,426, and 7,458,991, and U.S. Patent Application Nos. 2006/0147332 and 2006/0228247, the disclosures of which are all hereby incorporated by reference in their entireties. It is understood that all embodiments of the inventions described herein may utilize any combination of bone growth agents or structures to promote initial fixation and subsequent bone ongrowth and/or ingrowth.

Likewise, the various implants discussed herein may be formed of any suitable material for use in human implantation. For instance, embodiments are described above as being formed of metallic or polymeric material. However, the specific materials noted above should not be considered exhaustive of those that can be utilized. Indeed, other suitable materials may be employed in connection with the various implants. For instance, in embodiments where a polymeric material is identified, other suitable polymeric materials may be substituted. It is contemplated to utilize the materials and material combinations taught in U.S. Patent Application Publication No. 2010/0312348, the disclosure of which is hereby incorporated by reference herein.

Although described for specific uses above, the inventions described herein may used in other knee implant prosthesis designs including: focal defect repairs, bicondylar, bi-cruciate retaining, total knee replacements, revision knee replacements or hinged knee replacements. The inventions may also be used in any large or small articulating joints with the body including but not limited to: hip, shoulder, knee, hand, wrist, ankle or vertebral. Regarding spinal applications, this technology may be applied to vertebral body replacement devices, interbody spacers or articulating prostheses for any region of the spine including: lumbar, thoracic or cervical. This technology may further be applied in trauma or craniomaxillofacial applications.

Various embodiments of inventions have been described herein and it is understood that any of the features, or any combinations of any of the features, may be used in any alternate embodiments of a prosthetic implant. For example, any embodiment of a patello-femoral or unicondylar implant described herein may utilize a theoretical peg center as a geometric reference as opposed to a physical primary peg feature, which contains a primary peg center. Moreover, although certain specific structural aspects of certain preferred embodiments are shown and discussed herein, those preferred embodiments may vary while remaining squarely within the purview of the present invention. For instance, certain embodiment implants are shown as having specifically shaped fixation elements (e.g., cylindrical pegs). However, those elements may be modified according to the present invention (e.g., cylindrical pegs may be modified so as to be differently shaped pegs, keels can be substituted for the cylindrical pegs, etc. . . . ).

In addition, as mentioned above, the various prepared bone surfaces described herein may be formed through the use of many different means. For instance, traditional cutting or milling operations may be employed, as can the use of a cutting or milling instrument coupled with a robot or the like. Suitable robots may include the robotic systems described in U.S. Pat. Nos. 6,676,669; 7,892,243; 6,702,805; 6,723,106; 6,322,567; 7,035,716; 6,757,582; 7,831,292; 8,004,229; 8,010,180; 6,204,620; 6,313,595; and 6,612,449; U.S. Patent Application Nos. 2010/0268249; 2008/0202274; 2010/0268250; 2010/0275718; 2003/0005786; and U.S. Provisional Application No. 61/530,614 filed Nov. 16, 2011, the disclosures of which are hereby incorporated by reference herein. Likewise, such robots or similar robots may be utilized in placing any of the above-discussed implants on the bone. In either case, particular robotic system employed may include the use of a surgical system, such as is disclosed in U.S. Pat. No. 7,725,162 ("the '162 patent"), the disclosure of which is hereby incorporated by reference herein. In particular, the '162 patent discloses a navigation system that may be utilized in guiding a robotic system with respect to a bone or other anatomical structure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of arthroplasty comprising:
creating a resected bone surface of a bone;
preparing a first cavity extending into the resected bone surface, the first cavity having an arcuate longitudinal curvature;
preparing a second cavity in the resected bone surface providing a prosthetic implant having an articular surface, a bone contacting surface, and a first peg extending from the bone contacting surface, the first peg having an arcuate longitudinal curvature;
inserting a pivot surface of an end of the prosthetic implant into the second cavity until the pivot surface contacts the resected bone surface; and
coupling the prosthetic implant to the bone by pivoting the prosthetic implant about the pivot surface while the pivot surface remains in contact with the resected bone surface such that the first peg enters the first cavity.

2. The method of claim 1, wherein the creating step includes utilizing a cutting tool coupled with a robot.

3. The method of claim 1, further comprising the step of preparing a third cavity extending into the resected bone surface.

4. The method of claim 3, wherein the implant includes a second peg extending from a concave portion of the bone contacting surface and having a curved surface, the curved surface of the second peg concentrically curved with the arcuate longitudinal curvature of the first peg about a point on the pivot surface, and the implanting step includes disposing the curved surface of the second peg within the third cavity.

5. The method of claim 3, wherein the implant includes a second peg extending from a concave portion of the bone contacting surface and having a curved surface, the curved surface of the second peg and the arcuate longitudinal curvature of the first peg being non-concentrically curved with respect to one another, and the implanting step includes disposing the curved surface of the second peg within the third cavity.

6. The method of claim 1, wherein the first peg includes a first curved surface and a second curved surface.

7. The method of claim 6, wherein the step of preparing the first cavity includes preparing the first cavity to include a third curved surface corresponding to the first curved surface of the first peg and a fourth curved surface corresponding to the second curved surface of the first peg.

8. The method of claim 7, wherein the first and second curved surfaces of the first peg and the third and fourth curved surfaces of the first cavity are concentric with respect to one another after the implant is coupled to the bone.

9. The method of claim 7, wherein after the step of inserting the pivot surface of the prosthetic implant into the second cavity and before the step of coupling the implant to the bone, the first and second curved surfaces of the first peg are curved about a first point and the third and fourth curved surfaces of the first cavity are curved about a second point, the first and second points being different.

10. The method of claim 1, wherein the implant further includes a first projection.

11. The method of claim 10, further comprising the step of creating a first divot in the bone.

12. The method of claim 11, wherein the implanting step includes disposing the first projection within the first divot.

13. The method of claim 12, further comprising the step of creating a second divot in the bone and wherein the implanting step includes disposing the first projection within the second divot.

14. The method of claim 13, wherein the first projection is first positioned in within the first divot, and then the first projection is next positioned within the second divot.

15. The method of claim 10, wherein the first projection is ball shaped.

16. The method of claim 1, wherein the bone contacting surface includes a flat portion defining a first plane, the pivot surface located on the first plane.

17. The method of claim 1, wherein the implanting step is performed through the use of a robot.

\* \* \* \* \*